(12) United States Patent
Heinz et al.

(10) Patent No.: US 8,835,715 B1
(45) Date of Patent: Sep. 16, 2014

(54) PLANTS EXPRESSING Δ6-DESATURASE GENES AND OILS FROM THESE PLANTS CONTAINING PUFAS AND METHOD FOR PRODUCING UNSATURATED FATTY ACIDS

(75) Inventors: Ernst Heinz, Hamburg (DE); Thomas Girke, Riverside, CA (US); Jodi Scheffler, Stoneville, MS (US); Oswaldo Da Costa E Silva, Grenzach-Wyhlen (DE); Hermann Schmidt, Hamburg (DE); Ulrich Zähringer, Ahrensburg (DE); Ralf Reski, Oberried (DE)

(73) Assignee: BASF Plant Science GmbH, Ludwigshafen (DE)

( * ) Notice: Subject to any disclaimer, the term of this patent is extended or adjusted under 35 U.S.C. 154(b) by 754 days.

(21) Appl. No.: 10/019,048

(22) PCT Filed: Jul. 4, 2000

(86) PCT No.: PCT/EP00/06223
§ 371 (c)(1),
(2), (4) Date: Dec. 27, 2001

(87) PCT Pub. No.: WO01/02591
PCT Pub. Date: Jan. 11, 2001

(30) Foreign Application Priority Data

Jun. 30, 2000 (DE) .................................. 100 30 976

(51) Int. Cl.
*C12N 15/87* (2006.01)
*C12P 21/06* (2006.01)
*C07H 21/04* (2006.01)

(52) U.S. Cl.
USPC .......................................... 800/281; 435/69.1

(58) Field of Classification Search
USPC ........... 435/68.1, 70.1, 71.1, 183, 252.3, 419, 435/254
See application file for complete search history.

(56) References Cited

U.S. PATENT DOCUMENTS

| | | | |
|---|---|---|---|
| 5,504,200 | A | 4/1996 | Hall et al. |
| 5,608,152 | A | 3/1997 | Kridl et al. |
| 5,614,393 | A | 3/1997 | Thomas et al. |
| 8,022,272 | B2 * | 9/2011 | Heim et al. .................... 800/295 |

FOREIGN PATENT DOCUMENTS

| | | | |
|---|---|---|---|
| DE | 19828850 A1 * | 12/1999 | ............ C12N 15/53 |
| EP | 249 676 | 12/1987 | |
| EP | 335 528 | 10/1989 | |
| EP | 388 186 | 9/1990 | |
| EP | 550 162 | 7/1993 | |
| EP | 794 250 | 9/1997 | |
| WO | 91/13972 | 9/1991 | |
| WO | 91/13980 | 9/1991 | |
| WO | 93/06712 | 4/1993 | |
| WO | 93/11245 | 6/1993 | |
| WO | 93/21334 | 10/1993 | |
| WO | 94/11516 | 5/1994 | |
| WO | 94/18337 | 8/1994 | |
| WO | 95/15389 | 6/1995 | |
| WO | 95/18222 | 7/1995 | |
| WO | 95/19943 | 7/1995 | |
| WO | 95/23230 | 8/1995 | |
| WO | 96/21022 | 7/1996 | |
| WO | 97/21340 | 6/1997 | |
| WO | 97/30582 | 8/1997 | |
| WO | 98/45461 | 10/1998 | |
| WO | 98/46763 | 10/1998 | |
| WO | 98/46764 | 10/1998 | |
| WO | 98/46765 | 10/1998 | |
| WO | 98/46776 | 10/1998 | |
| WO | 99/16890 | 4/1999 | |
| WO | 99/27111 | 6/1999 | |
| WO | 99/64616 | 12/1999 | |
| WO | 00/12720 | 3/2000 | |
| WO | 00/21557 | 4/2000 | |
| WO | WO 00/00593 * | 6/2000 | ............ C12N 15/53 |

OTHER PUBLICATIONS

Merck Index, Tenth Edition, Windholz et al., eds., Merck and Co., Inc., NJ, 1983; compound 5333.*
Attwood. Science. 2000; 290: 471-3.*
Berendsen. Science. 1998; 282:642-3.*
Galperin et al. Nat. Biotech. 2000; 18:609-13.*
Girke et al. Plant J. 1998; 15: 39-48.*
Hongsthong et al. Appl. Microbiol. Bioteh. 2004; 66:74-84.*
Kinney et al. Biochem. Soc. Trans., 2002; 30:1099-1103.*
Laoteng et al. Biochem. Biophys. Res. Comm. 2000; 279: 17-22.*
Napier et al. Curr. Opin. Plant Bio. 1999; 2: 123-27.*
Reddy et al. Nat. Biotech. 1996; 14: 639-42.*
Sakuradani et al. Biosci. Biotech. Biochem. 2003; 67:704-11.*
Sayanova et al. 2000; 28 :636-38.*
Sayanova et al. J. Exp. Botany, 2001; 52: 1581-5.*
Spychalla et al. Proc. Natl. Acad. Sci. 1997; 94: 1142-47.*
Pohl et al., J. Biotech., 2006, vol. 124, pp. 26-40.*
Score report SEQ No. 1 result (Sep. 23, 2005).*
Score report SEQ No. 2 result (Sep. 23, 2005).*

(Continued)

*Primary Examiner* — Catherine Hibbert
(74) *Attorney, Agent, or Firm* — Drinker Biddle & Reath LLP

(57) ABSTRACT

The present invention relates to an improved process for the preparation of unsaturated fatty acids and to a process for the preparation of triglycerides with an increased content of unsaturated fatty acids. The invention relates to the generation of transgenic organism, preferably of a transgenic plant or of a transgenic microorganism, with an increased content of fatty acids, oils or lipids with Δ6 double bonds owing to the expression of a moss Δ-6-desaturase [sic].

Figure 3B:
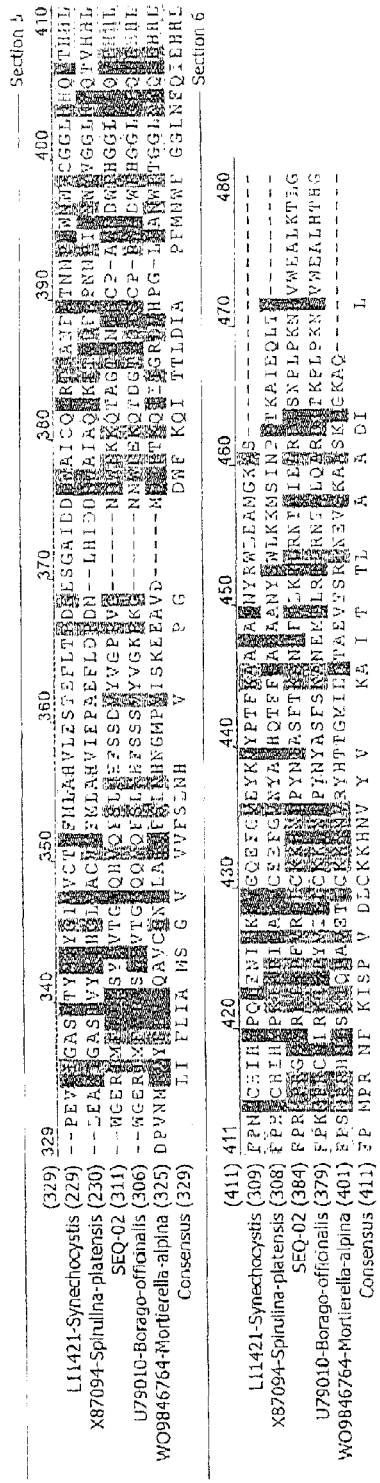
Figure 6:
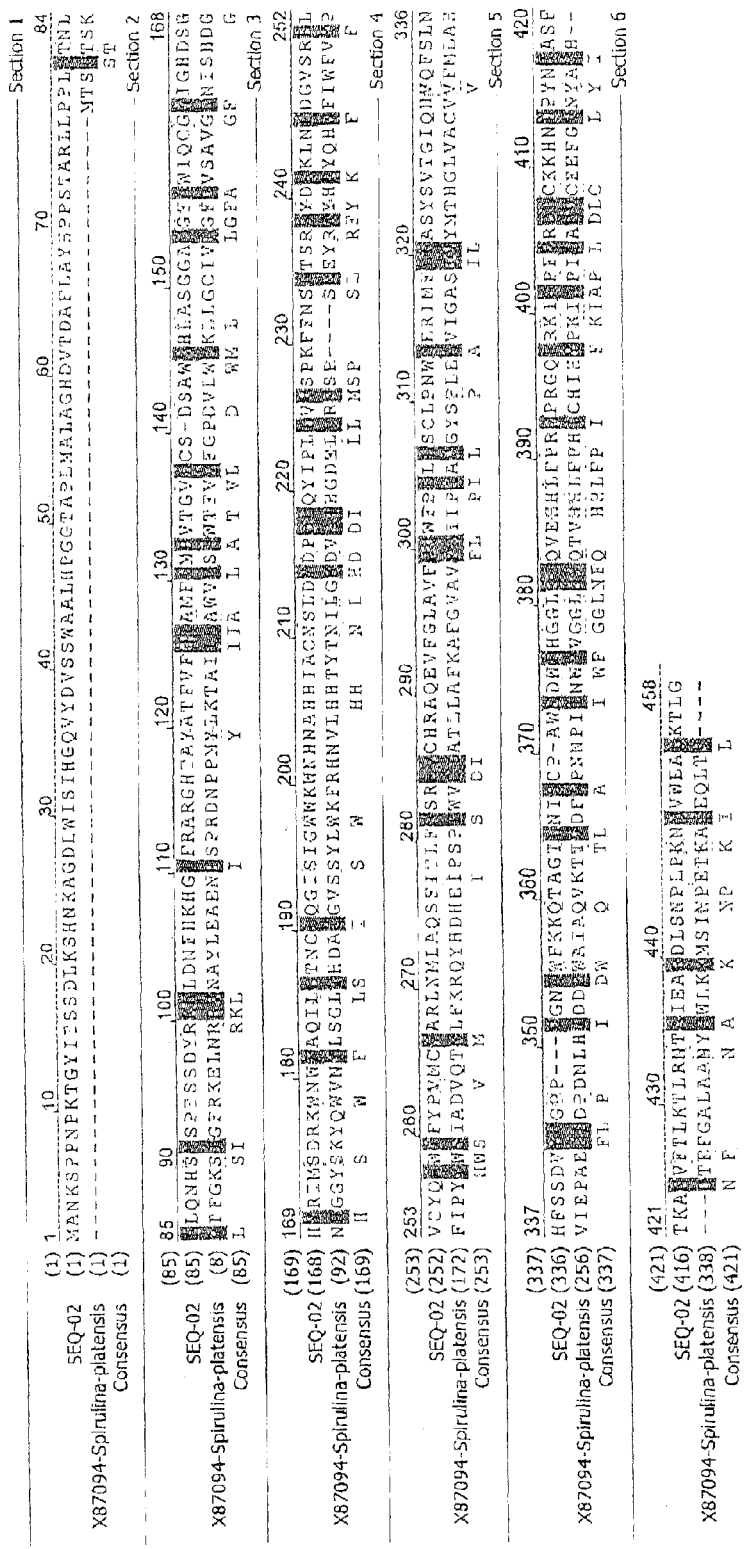
Figure 7:
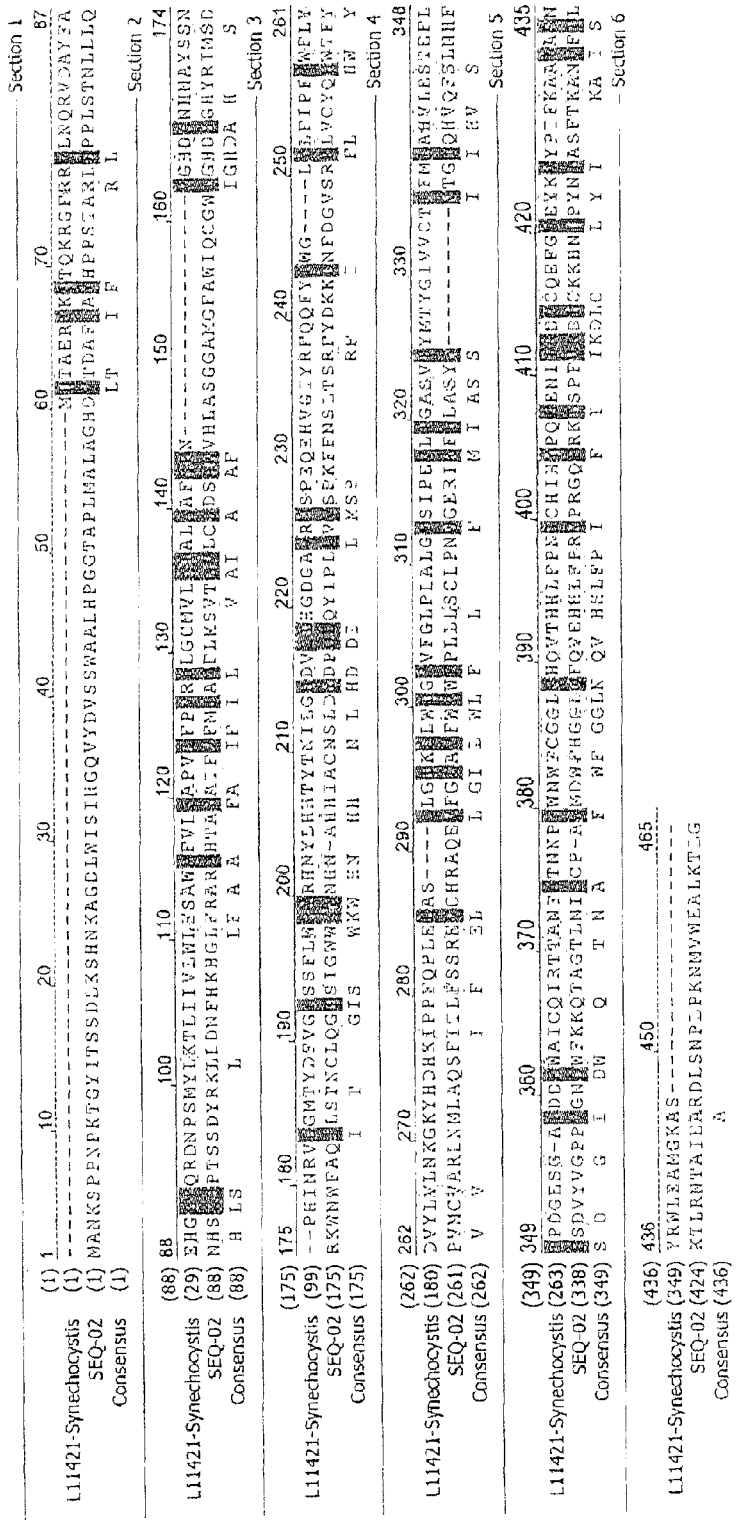

The invention furthermore relates to transgenic organisms comprising a Δ6-desaturase gene, and to the use of the unsaturated fatty acids or of the triglycerides with an increased content of unsaturated fatty acids prepared in the process.

7 Claims, 8 Drawing Sheets

(56) References Cited

OTHER PUBLICATIONS

Score Report "Result 2" submitted as a direct submission by author T. Girke on Dec. 19, 1997 (University Hamburg).*
Reddy and Thomas in "Expression of a cyanobacterial delta6-desaturase gene results in gamma-linolenic acid production in transgenic plants" (Nature Biotechnology, vol. 14, May 1996; pp. 639-642).*
Sperling et al in "A bifunctional Δ6-fatty acyl acetylenase/desaturase from the moss *Ceratodon purpureus*" (Eur J Biochem: 2000, vol. 267, pp. 3801-3811, published Jun. 2000).*
Murata et al., Biosynthesis of γ-linolenic acid in cyanobacterium *Spirulina patensis*, pp. 22-32, In: γ-linolenic acid, metabolism and its roles in nutrition and medicine, Huang, Y. and Milles, D.E. [eds.], AOC Press, Champaign, Illinois.
van den Hondel et al., Heterologous gene expression in filamentous fungi, 1991 in: More Gene Manipulations in Fungi, J.W. Bennet & L.L: Lasure, eds., pp. 396-428, Academic Press: San Diego.
Girke et al., Plant J. 15, 1998 : 39-48.
Napier et al., Biochem. J., 330, 1998: 611-614.
Sayanova et al., Proc. Natl. Acad. Sci., USA, 94, 1997: 4211-4216.
Cho et al., J. Biol. Chem., 274, 1999: 471-477.
Aki et al., Biochem. Biophys. Res. Commun., 255 1999 : 575-579.
Reddy et al., Plant. Mol. Biol., 27, 1993 : 293-300.
Stukey et al., J. Biol. Chem., 265, 1990: 20144-20149.
Huang et al., Lipids, 34, 1999: 649-659.
Wada et al., Nature, 347, 1990: 200-203.
Wang et al., Plant Physiol. Biochem., 26, 1988: 777-792.
McKeon et al., Methods in Enzymol., 71, 1981: 12141-12147.
Baeumlein et al., Mol. Gen. Genet., 225 (3), 1991: 459-467.
Baeumlein et al., Plant J., 2, 2, 1992: 233-239.
Stockhaus et al., EMBO J., 8, 1989: 2445-2450.
Gatz et al., Plant J., 2, 1992: 397-404.
Deverux et al., Nucleic. Acid Res., 12, 1984: 387-395.
J. Mol. Evolution, 25, 1987: 351-360.
Higgins et al., CABIOS, 5, 1989: 151-153.
Franck et al., Cell, 21, 1980: 285-294.
Ward et al, Plant. Mol. Biol., 22, 1993: 361-366.
van den Hondel and Punt 1991, in: Applied Molecular Genetics of Fungi, Peberdy et al., eds., pp. 1-28, Cambridge University Press: Cambridge.
Romanos et al., Foreign gene expression in yeast: a review, Yeast, 8, 1992: 423-488.
Kermode et al., Crit. Rev. Plant Sci., 15, 4, 1996: 285-423.
Gallie et al., Nucl. Acid. Res., 15, 1987: 8693-8711.
Schouten et al., Plant. Mol. Biol., 30, .1996: 781-792.
Gielen et al., EMBO J. 3, 1984: 835 ff.
Wada et al., Nucleic. Acid. Res., 20, 1992: 2111-2118.
Patten et al., Current Opinion in Biotechnology, 8, 1997: 724-733.
Moore et al., J. Mol. Biol., 272, 1997: 336-347

* cited by examiner

PLANTS EXPRESSING Δ6-DESATURASE GENES AND OILS FROM THESE PLANTS CONTAINING PUFAS AND METHOD FOR PRODUCING UNSATURATED FATTY ACIDS

RELATED APPLICATIONS

This application is a national stage application (under 35 U.S.C. §371) of PCT/EP00/06223, filed Jul. 4, 2000, which claims benefit of U.S. application Ser. No. 09/347,531, filed Jul. 6, 1999 and German Application 100 30 976.3, filed Jun. 30, 2000.

The invention furthermore relates to transgenic organisms containing a Δ6-desaturase gene, and to the use of the unsaturated fatty acids or triglycerides with an increased content of unsaturated fatty acids which have been prepared by the process.

Fatty acids and triglycerides have a multiplicity of uses in the food industry, in livestock nutrition, in cosmetics and in the pharmaceutical sector. They are suitable for a wide variety of uses depending on whether they are free saturated or unsaturated fatty acids or triglycerides with an increased content of saturated or unsaturated fatty acids; thus, for example, polyunsaturated fatty acids are added to baby food to increase the nutritional value. The various fatty acids and triglycerides are obtained mainly from microorganisms such as *Mortierella* or from oil-producing plants such as soybean, oilseed rape, sunflower and others, usually, resulting in the form of their triacyl glycerides. However, they can also be obtained from animal species such as fish. The free fatty acids are advantageously prepared by saponification.

Depending on the intended use, oils with saturated or unsaturated fatty acids are preferred; thus, for example, lipids with unsaturated fatty acids, specifically polyunsaturated fatty acids, are preferred in human nutrition because they have a beneficial effect on the blood cholesterol level and thus on the possibility of heart disease. A positive action on carcinogenesis is also attributed to the unsaturated fatty acids. Moreover, they are important starting materials for the synthesis of compounds which govern important biological processes within the organism. They are therefore used in various dietetic foodstuffs or medicaments.

Owing to their beneficial properties, there has been no lack of attempts in the past to make available genes which are involved in the synthesis of fatty acids or triglycerides for the production of oils in various organisms with a modified content of unsaturated fatty acids. Thus, a Δ9-desaturase is described in WO 91/13972 and its US equivalent. WO 93/11245 claims a Δ15-desaturase, while WO 94/11516 claims a Δ12-desaturase. Δ6-desaturases are described in Girke et al. (The Plant Journal, 15, 1998: 39-48), Napier et al. (Biochem. J., 330, 1998: 611-614), Murata et al. (Biosynthesis of γ-linolenic acid in cyanobacterium *Spirulina patensis*, pp. 22-32, In: γ-linolenic acid, metabolism and its roles in nutrition and medicine, Huang, Y. and Milles, D. E. [eds.], AOC Press, Champaign, Ill.), Sayanova et al. (Proc. Natl. Acad. Sci. USA, 94, 1997: 4211-4216), WO 98/46764, Cho et al. (J. Biol. Chem., 274, 1999: 471-477), Aki et al. (Biochem. Biophys. Res. Commun., 255, 1999: 575-579), and Reddy et al. (Plant Mol. Biol., 27, 1993: 293-300). Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. Further Δ6-desaturase are described in WO 93/06712, U.S. Pat. No. 5,614,393, U.S. Pat. No. 5,614,393, WO 96/21022, WO 00/21557 and WO 99/27111. The biochemical characterization of the various desaturases is, however, inadequate as yet because the enzymes, being membrane-bound proteins, can be isolated and characterized only with great difficulty (McKeon et al., Methods in Enzymol. 71, 1981: 12141-12147, Wang et al., Plant Physiol. Biochem., 26, 1988: 777-792). As a rule, membrane-bound desaturases are characterized by introducing them into a suitable organism which is subsequently tested for enzyme activity by analyzing the starting material and the product. The use for production in transgenic organisms described as in WO 98/46763 WO 98/46764, WO 98/46765. The expression of various desaturases as in WO 99/64616 or WO 98/46776 and the formation of polyunsaturated fatty acids is also described and claimed here. As regards the expression efficacy of desaturases and their effect on the formation of polyunsaturated fatty acids, it must be noted that expression of an individual desaturase as described in the above prior art only led to, and leads to, low contents of unsaturated fatty acids, for example Δ6-unsaturated fatty acids/lipids such as, for example, γ-linoleic acid, being achieved.

There is thus still a great need for novel genes which are better suited and which encode enzymes which are involved in the biosynthesis of unsaturated fatty acids and which allow them to be produced on an industrial scale. Furthermore, there is still a need for improved methods of obtaining the highest possible contents of polyunsaturated fatty acids.

It is an object of the present invention to provide a process for the preparation of unsaturated fatty acids using genes which encode, for example, desaturase enzymes and which are involved in the synthesis of polyunsaturated fatty acids in the seeds of an oil crop, thus increasing the content of polyunsaturated fatty acids.

We have found that this object is achieved by a process for the preparation of unsaturated fatty acids, which comprises introducing, into an organism, at least one isolated nucleic acid sequence encoding a polypeptide having Δ6-desaturase activity, selected from the group consisting of:
a) a nucleic acid sequence having the sequence shown in SEQ ID NO: 1,
b) nucleic acid sequences which, as a result of the degeneracy of the genetic code, are derived from the sequence shown in SEQ ID NO: 1,
c) derivatives of the nucleic acid sequence shown in SEQ ID NO: 1 which encode polypeptides with the amino acid sequences shown in SEQ ID NO: 2 and have at least 50% homology at the amino acid level without substantially reducing the enzymatic action of the polypeptides, and culturing this organism, where the cultured organism contains at least 1 mol % of unsaturated fatty acids based on the total fatty acid content in the organism.

Culturing this organism means both growing plants and culturing eukaryotic or prokaryotic microorganisms such as bacteria, yeasts, fungi, ciliates, algae, cyanobacteria, animal or plant cells or cell associations, or rearing animals.

The organisms obtained by the processes according to the invention contain, as a rule, unsaturated fatty acids in the form of bound fatty acids, i.e. the unsaturated fatty acids exist predominantly in the form of their mono-, di- or triglycerides, glycolipids, lipoproteins or phospholipids such as oils or lipids or else as fatty acids bound as esters or amides. Free fatty acids are also present in the organisms in the form of the free fatty acids or in the form of their salts. Advantageously, the free or bound unsaturated fatty acids have an increased content of fatty acids with Δ6 double bonds, such as, advantageously, γ-linoleic acid, which is increased over that of the starting organisms. The organisms obtained by culturing in the process according to the invention, and the unsaturated fatty acids which they contain, can be used directly, for example for the production of pharmaceutical products, of agrochemicals, feeds or foodstuffs or else after isolation from the organisms. All steps of the purification of the unsaturated fatty acids can be used, that is to say that all steps from crude extracts of the fatty acids up to fully purified fatty acids are suitable for preparing the abovementioned products. In an advantageous embodiment, the bound fatty acids can be liberated from the for example, oils or lipids for example by hydrolysis with bases, such as, for example, with NaOH or KOH. These free fatty acids can be used directly in the mixture obtained or after further purification for producing pharmaceutical products, agrochemicals, feeds of foodstuffs. Also, the bound or free fatty acids can be used for transesterification or esterification, for example with other mono, di- or triglycerides or glycerol in order to increase the content of unsaturated fatty acids in these compounds, for example in the triglycerides.

The invention furthermore relates to a process for the preparation of triglycerides with an increased content of unsaturated fatty acids by incubating triglycerides with saturated or unsaturated or saturated and unsaturated fatty acids with at least one of the proteins encoded by the sequence SEQ ID NO: 2. The processes are advantageously carried out in the presence of compounds which are capable of accepting or donating reduction equivalents. The fatty acids can subsequently be released from the triglycerides.

The abovementioned methods advantageously allow fatty acids of bound fatty acids such as triglycerides with an increased content of fatty acids with Δ6 double bonds to be synthesized.

Organisms which may be mentioned for the abovementioned processes are, for example, plants such as *Arabidopsis*, barley, wheat, rye, oats, maize, soybean, rice, cotton, sugarbeet, tea, carrot, *capsicum*, canola, sunflower, flax, hemp, potato, triticale, tobacco, tomato, oilseed rape, coffee, tapioca, carcaba, arrowroot, tagetes, alfalfa, peanut, castor, coconut, oilpalm, safflower (*Carthamus tinctorius*), lettuce and the various tree, nut and grapevine species, or cacao bean, microorganisms such as the fungi *Mortierella, Saprolegnia* or *Pythium*, bacteria such as the genus *Escherichia*, cyanobacteria, algae or protozoans such as dinoflagellates such as Crypthecodinium. Preferred organisms are those which are naturally capable of synthesizing substantial amounts of oils, such as microorganisms such as fungi such as *Mortierella alpina, Pythium insidiosum* or plant such as soybean, oilseed rape, coconut, oil palm, canola, safflower (*Carthamus tinctorius*), castor, *calendula*, linseed, borage, peanut, cacao bean or sunflower, with soybean, oilseed rape or sunflower being especially preferred.

Depending on the host organism, the organisms used in the processes are cultured or grown in the manner known to the skilled worker. Microorganisms, such as bacteria, fungi, ciliates, plant or animal cells, are usually cultured in a liquid medium which contains a carbon source, in most cases in the form of sugars, a nitrogen source, in most cases in the form of organic nitrogen sources such as yeast extract or salts such as ammonium sulfate, trace elements such as iron salts, manganese salts and magnesium salts and, if appropriate, vitamins, at temperatures between 0° C. and 100° C., preferably between 10° C. and 60° C., either with passing in of oxygen or in the absence of oxygen, depending on the organism. It is possible in this context to maintain the pH of the medium at a fixed value, that is to say the pH is regulated during culturing or else the pH is not regulated and changes during culture. Culturing can be carried out batchwise, semi-batchwise or continuously. Nutrients can be introduced at the beginning of the fermentation or subsequently fed semicontinuously or continuously. A culture on solid media is also possible.

After the transformation, plants are, as a rule, first regenerated and then cultured or grown as customary. This can be done in the greenhouse or in the open.

After cultivation, the lipids are obtained from the organisms in the customary manner. To this end, the organisms can first be disrupted after harvesting or else used directly. The lipids are advantageously extracted with suitable solvents such as apolar solvents such as hexane or ethanol, isopropanol or mixtures such as hexane/isopropanol, phenol/chloroform/isoamyl alcohol at temperatures between 0° C. to 80° C., preferably between 20° C. to 50° C. As a rule, the biomass is extracted with an excess of solvent, for example an excess of solvent to biomass of 1:4. The solvent is subsequently removed, for example via distillation. Extraction can also be effected by using supercritical $CO_2$. After extraction, the residual biomass can be removed for example by filtration.

The crude oil thus obtained can subsequently be purified further, for example by removing cloudiness by treating the oil with polar solvents such as acetone or chloroform, followed by filtration or centrifugation. A further purification by chromatographic methods, distillation or crystallization is also possible.

To obtain the free fatty acids from the triglycerides, they are saponified in the customary manner as described above.

The invention furthermore relates to unsaturated fatty acids and to triglycerides with an increased content of unsaturated fatty acids which have been prepared by the abovementioned methods, and to their use for the production of foodstuffs, feeds, cosmetics or pharmaceuticals. To this end, they are added in customary quantities to the foodstuffs, the feeds, the cosmetics or the pharmaceuticals.

In the process according to the expression, higher contents of unsaturated fatty acids such as γ-linolenic acid were obtained by expressing a moss Δ6-desaturase in organisms such as fungi, bacteria, animal or plants, preferably fungi, bacteria and plants, especially preferably in plants, very especially preferably in oil crops such as oilseed rape, canola, linseed, soybean, sunflower, borage, castor, oilpalm, safflower (*Carthamus tinctorius*), coconut, peanut or cacao bean. Expression in field crops such as maize, wheat, rye, oats, triticale, rice, barley, alfalfa or bush plants (coffee, cacao, tea) is also advantageous. Expression in the abovementioned organisms of a gene which encodes a moss Δ6-desaturase allows contents of unsaturated fatty acids of at least 1 mol %, preferably at least 3 mol %, especially preferably at least 4 mol %, very especially preferably at least 5 mol %, to be achieved in the organisms.

Derivative(s) are to be understood as meaning, for example, functional homologues of the enzymes encoded by SEQ ID NO: 1 or their enzymatic activity, that is to say enzymes which catalyze the same enzymatic reactions as those of SEQ ID NO: 1. These genes also make it possible advantageously to prepare unsaturated fatty acids with double bonds in position Δ6. Unsaturated fatty acids are to be understood hereinbelow as meaning doubly or polyunsaturated fatty acids which have double bonds. The double bonds can be conjugated or unconjugated. The sequence stated in SEQ ID NO: 1 encodes an enzyme which has a Δ6-desaturase activity.

The enzyme Δ6-desaturase according to the invention advantageously introduces a cis double bond in position $C_6$-$C_7$ into fatty acid residues of glycerolipids (see SEQ ID NO: 1). Moreover, the enzyme has a Δ6-desaturase activity which advantageously introduces exclusively a cis double bond in position $C_6$-$C_7$ into fatty acid residues of glycerolipids. The enzyme with the sequence stated in SEQ ID NO: 1 also has this activity, which is that of a monofunctional Δ6-desaturase.

The nucleic acids sequence(s) (the singular is intended to encompass the plural, and vice versa, for the application) or fragments thereof used in the process according to the invention can be used advantageously for isolating further genomic sequences via homology screening.

The derivatives mentioned can be isolated, for example, from other organisms, for example eukaryotic organisms such as plants, such as, especially, mosses, dinoflagellates or fungi.

Derivatives or functional derivatives of the sequence stated in SEQ ID NO: 1 are furthermore to be understood as meaning, for example, allelic variants which have at least 50% homology at the deduced amino acid level, advantageously at least 70% homology, preferably at least 80% homology, especially preferably at least 85% homology, and very especially preferably 90% homology. The homology was calculated over the entire amino acid region. The program PileUp, BESTFIT, GAP, TRANSLATE or BACKTRANSLATE (=constituent of the program package UWGCG, Wisconsin Package, Version 10.0-UNIX, January 1999, Genetics Computer Group, Inc., Deverux et al., Nucleic. Acid Res., 12, 1984: 387-395) was used (J. Mol. Evolution., 25, 351-360, 1987, Higgins et al., CABIOS, 5 1989: 151-153). The amino acid sequences deduced from the specified nucleic acids can be found in sequence SEQ ID NO: 2. Homology is to be understood as meaning identity, i.e. the amino acid sequences are at least 50% identical. The sequences according to the invention have at least 65%, preferably at least 70%, especially preferably 75%, very especially preferably at least 80%, homology at the nucleic acid level.

Allelic variants, comprise, in particular, functional variants which can be obtained from the sequence shown in SEQ ID NO: 1 by deletion, insertion or substitution of nucleotides, while retaining the enzymatic activity of the deduced synthesized proteins.

Such DNA sequences can be isolated starting from the DNA sequence described in SEQ ID NO: 1 or parts of these sequences from other eukaryotes, such as, for example, those mentioned above, for example using customary hybridization methods or the PCR technique. These DNA sequences hybridize with the abovementioned sequences under standard conditions. For hybridization, it is advantageous to use short oligonucleotides, for example of conserved regions, which can be determined in a manner known to the skilled worker by comparisons with other desaturase genes. It is advantageous to use the histidine box sequences. However, it is also possible to use longer fragments of the nucleic acids according to the invention or the complete sequences for the hybridization. These standard conditions vary depending on the nucleic acid used: oligonucleotide, longer fragment or complete sequence, or depending on which type of nucleic acid, DNA or RNA, is used for the hybridization. Thus, for example, the melting temperatures for DNA:DNA hybrids are about 10° C. lower than those for DNA:RNA hybrids of the same length.

Standard conditions mean, for example, depending on the nucleic acid, temperatures between 42 and 58° C. in an aqueous buffer solution with a concentration between 0.1 and 5×SSC (1×SSC=0.15 M NaCl, 15 mM sodium citrate, pH 7.2) or additionally in the presence of 50% formamide, such as, for example, 42° C. in 5×SSC, 50% formamide. The hybridization conditions for DNA:DNA hybrids are advantageously 0.1×SSC and temperatures between about 20° C. and 45° C., preferably between about 30° C. and 45° C. The hybridization conditions for DNA:RNA hybrids are advantageously 0.1×SSC and temperatures between about 30° C. to [sic] and 55° C., preferably between about 45° C. and 55° C. These temperatures stated for the hybridization are melting temperatures calculated by way of example for a nucleic acid with a length of about 100 nucleotides and a G+C content of 50% in the absence of formamide. The experimental conditions for DNA hybridization are described in relevant textbooks of genetics such as, for example, Sambrook et al., "Molecular Cloning", Cold Spring Harbor Laboratory, 1989, and can be calculated by the formulae known to the skilled worker, for example depending on the length of the nucleic acids, the nature of the hybrids or the G+C content. Further information on hybridization can be found by the skilled worker in the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

Derivatives are also to be understood as meaning homologues of the sequence SEQ ID No: 1, for example eukaryotic homologues, truncated sequences, single-stranded DNA of the coding and noncoding DNA sequence or RNA of the coding and noncoding DNA sequence.

Homologues of the sequence SEQ ID NO: 1 are furthermore to be understood as meaning derivatives such as, for example, promoter variants. These variants can be modified by one or more nucleotide exchanges, by insertion(s) and/or deletion(s), but without adversely affecting the functionality or efficacy of the promoters. Moreover, the promoters may have their efficacy increased by modification of their sequence, or be completely replaced by more effective promoters, even from heterologous organisms.

Derivatives are also advantageously understood as meaning variants whose nucleotide sequence in the region from −1 to −2000 in front of the start codon has been modified so that gene expression and/or protein expression is altered, preferably increased. Moreover, derivatives are also understood as meaning variants which have been modified at the 3' end.

The nucleic acid sequences encoding a Δ6-desaturase can be synthesized or obtained from nature or contain a mixture of synthetic or natural DNA constituents, or else be composed of various heterologous Δ6-desaturase gene sections from various organisms. In general, synthetic nucleotide sequences are produced using codons which are preferred by the host organisms in question, for example plants. As a rule, this leads to optimal expression of the heterologous genes. These codons which are preferred by plants may be determined from codons with the greatest protein frequency which are expressed in most plant species of interest. An example for *Corynebacterium glutamicum* is given in: Wada et al. (1992) *Nucleic Acids Res.* 20:2111-2118). Experiments of this type can be carried out by standard methods and are known to those skilled in the art.

Functionally equivalent sequences encoding the Δ6-desaturase gene are those derivatives of the sequence according to the invention which still have the desired functions, i.e. the enzymatic activity of the proteins, despite deviating nucleotide sequence. Functional equivalents thus encompass naturally occurring variants of the sequences described herein and artificial nucleotide sequences, for example obtained by chemical synthesis and adapted to the codon usage of a plant.

In addition, artificial DNA sequences are suitable as long as they confer, as described above, the desired property, for example the increase in the content of Δ6-double bonds in fatty acids, oils or lipids in the plant by overexpression of the Δ6-desaturase gene in crop plants. Such artificial DNA sequences, can be established for example, by backtranslation of proteins constructed by means of molecular modeling and having Δ6-desaturase activity, or by in-vitro selection. Techniques which are possible for the in-vitro evolution of DNA for modifying or improving the DNA sequences are described in Patten, P. A. et al., Current Opinion in Biotechnology 8, 724-733 (1997) or in Moore, J. C. et al., Journal of Molecular Biology 272, 336-347 (1997). Coding DNA sequences which have been obtained by backtranslating of a polypeptide sequence in accordance with the codon usage specific for the host plant are particularly suitable. This specific codon usage can be determined easily by a skilled worker familiar with methods of plant genetics by computer analysis of other, known genes of the plant to be transformed.

Further suitable equivalent nucleic acid sequences which must be mentioned are sequences which encode fusion proteins, where a Δ6-desaturase polypeptide or a functionally equivalent portion thereof is part of the fusion protein. The second portion of the fusion protein can be, for example, another polypeptide with enzymatic activity or an antigenic polypeptide sequence with the aid of which it is possible to detect Δ6-desaturase expression (for example myc-tag or his-tag). However, this preferably takes the form of a regulatory protein sequence such as, for example, an ER signal sequence, which guides the Δ6-desaturase protein to the desired site of action.

It is advantageously possible to combine the Δ6-desaturase gene in the process according to the invention with further genes of fatty acid biosynthesis. Examples of such genes are the acetyl transferases, further desaturases or elongases of unsaturated or saturated fatty acids as described in WO 00/12720. Advantageous for the in-vivo and, specifically, in-vitro synthesis is the combination with, for example, NADH cytochrome B5 reductases, which are able to accept or dominate reduction equivalents.

The proteins used in the process according to the invention are to be understood as meaning proteins which comprise an amino acid sequence shown in SEQ ID NO: 2 or a sequence which can be obtained therefrom by substitution, inversion, insertion or deletion of one or more amino acid residues, with the enzymatic activity of the protein shown in SEQ ID NO: 2 being retained or not substantially reduced. Not substantially reduced is to be understood as meaning all enzymes which still have at least 10%, preferably 20%, especially preferably 30%, of the enzymatic activity of the starting enzyme. It is moreover possible, for example, to replace particular amino acids by those with similar physico-chemical properties (bulk, basicity, hydrophobicity and the like). For example, arginine residues are replaced by lysine residues, valine residues by isoleucine residues or aspartic acid residues by glutamic acid residues. However, it is also possible for one or more amino acids to be transposed in their sequence, added or deleted, or several of these measures can be combined with each other.

Derivatives are also to be understood as functional equivalents which comprise, in particular, also natural or artificial mutations of an originally isolated sequence encoding a Δ6-desaturase and which additionally show the required function, that is to say the enzymatic activity is not substantially reduced. Mutations encompass substitutions, additions, deletions, transpositions or insertions of one or more nucleotide residues. Thus, for example, the present invention also extends to those nucleotide sequences which are obtained by modification of the Δ6-desaturase nucleotide sequence. The aim of such a modification may be, for example, to localize further the coding sequence contained therein or, for example, also to insert further restriction enzyme cleavage sites.

Functional equivalents are also those variants whose function is, compared with the initial gene or gene fragment, attenuated (=not substantially reduced) or enhanced (=enzyme activity is greater than the activity of the initial enzyme, that is to say the activity is over 100%, preferably over 110%, particularly preferably over 130%).

The nucleic acid sequences mentioned above which can be used in the process according to the invention are advantageously inserted into an expression cassette in order to introduce them into a host organism. However, the nucleic acid sequences can also be introduced directly into the host organism. The nucleic acid sequence may advantageously be, for example, a DNA or cDNA sequence.

Coding sequences which are suitable for insertion into an expression cassette are, for example, those which encode a Δ6-desaturase with the above-described sequences and which impart, to the host, the ability of overproducing fatty acids, oils or lipids with double bonds in position Δ6. These sequences can be of homologous or heterologous origin.

An expression cassette (=nucleic acid construct or fragment) is to be understood as meaning the sequence stated in SEQ ID NO: 1 which is the result of the genetic code and/or its functional or nonfunctional derivatives which have advantageously been linked functionally to one or more regulatory signals to increase gene expression and which control expression of the coding sequence in the host cell. These regulatory sequences are intended to make specific expression of the genes and protein expression possible. This may mean, for example, depending on the host organism, that the gene is expressed and/or overexpressed only after induction, or that it is expressed and/or overexpressed immediately. For example, these regulatory sequences are sequences to which inducers or repressors bind and thus regulate expression of the nucleic acid. In addition to these novel regulatory sequences or in place of these sequences, it is possible for the natural regulation of these sequences still to be present in front of the actual structural genes and, where appropriate, to have been genetically modified so that natural regulation has been switched off and expression of the genes has been increased. However, the gene construct may also have a simple structure, that is to say no additional regulatory signals have been inserted in front of the nucleic acid sequence or its derivatives and the natural promoter with its regulation has not been removed. Instead, the natural regulatory sequence has been mutated so that regulation no longer takes place and/or gene expression is increased. These modified promoters may also be placed alone in the form of subsequences (=promoter with parts of the nucleic acid sequences according to the invention) in front of the natural gene to increase the activity. In addition, the gene construct may advantageously comprise one or more enhancer sequences functionally linked to the promoter, which makes increased expression of the nucleic acid sequence possible. It is also possible to insert additional advantageous sequences at the 3' end of the DNA sequences, such as further regulatory elements or terminators. The Δ6-desaturase gene may be present in one or more copies in the expression cassette (=gene construct). Any genes which are coexpressed and which are advantageously involved in fatty acid biosynthesis may also be present in the expression cassette in one or more copies.

The regulatory sequences or factors may, as described above, preferably have a beneficial effect on the gene expression of the genes introduced, thus increasing it. Thus, enhancement of the regulatory elements can advantageously take place at the transcriptional level by using strong transcription signals such as promoters and/or enhancers. However, it is also possible to enhance translation by, for example, improving the stability of mRNA.

Suitable promoters in the expression cassette are, in principle, all promoters which are capable of controlling the expression of foreign genes in organisms, advantageously in plants of fungi. It is preferable to use in particular a plant promoter or promoters derived from, for example, a plant virus. Examples of advantageous regulatory sequences for the process according to the invention are present, for example, in promoters such as the cos, tac, trp, tet, trp-tet, lpp, lac, lpp-lac, lacI$^q$, T7, T5, T3, gal, trc, ara, SP6, 1-P$_R$ or in the 1-P$_L$ promoter which are advantageously used in Gram-negative bacteria. Further advantageous regulatory sequences are present, for example, in the Gram-positive promoters amy and SPO2, in the yeast or fungal promoters ADC1, MFα, AC, P-60, CYC1, GAPDH, TEF, rp28, ADH or in the plant promoters such as CaMV/35S [Franck et al., Cell 21 (1980) 285-294], RUBISCO SSU, OCS, B33, nos (=Nopaline Synthase Promoter) or in ubiquitin promoter. The expression cassette can also comprise a chemically inducible promoter by which expression of the exogenous Δ6-desaturase gene in the organisms, advantageously in the plants, can be controlled at a particular time. Examples of such advantageous plant promoters are the PRP1 promoter [Ward et al., Plant. Mol. Biol. 22 (1993), 361-366], a benzenesulfonamide-inducible promoter (EP 388186), a tetracycline-inducible promoter (Gatz et al., (1992) Plant J. 2, 397-404), a salicylic acid-inducible promoter (WO 95/19443), an abscisic acid-inducible promoter (EP335528) and an ethanol- or cyclohexanone-inducible promoter (WO 93/21334). Further plant promoters are, for example, the potato cytosolic FBPase promoter, the potato ST-LSI promoter (Stockhaus et al., EMBO J. 8 (1989) 2445-245), the *Glycine max* phosphoribosyl-pyrophosphate amidotransferase promoter (see also Genbank Accession Number U87999) or a node-specific promoter as are advantageously used in EP 249676. Particularly advantageous plant promoters are those which ensure expression in tissues or plant parts/organs in which fatty acid biosynthesis or its precursors take place, such as, for example, in the endosperm or the developing embryo. Particular mention should be made of advantageous promoters which ensure seed-specific expression, such as, for example, the USP promoter or derivatives thereof, the LEB4 promoter, the phaseolin promoter or the napin promoter. The USP promoter which has been stated in accordance with the invention and which is particularly advantageous, or its derivatives, mediate very early gene expression during seed development (Baeumlein et al., Mol Gen Genet, 1991, 225 (3): 459-67). Other advantageous seed-specific promoters which can be used for monocotyledonous and dicotyledonous plants are the promoters suitable for dicots such as, for example, the oilseed rape napin gene promoter (U.S. Pat. No. 5,608,152), the *Arabidopsis* oleosin promoter (WO98/45461), the *Phaseolus vulgaris* phaseolin promoter (U.S. Pat. No. 5,504,200), the *Brassica* Bce4 promoter (WO91/13980) or the legume B4 promoter (LeB4, Baeumlein et al., Plant J., 2, 2, 1992: 233-239) or promoters which are suitable for monocots, such as the barley lpt2- or lpt1-gene promoters (WO95/15389 and WO95/23230) or the promoters of the barley hordein gene, of the rice glutelin gene, of the rice oryzin gene, of the rice prolamin gene, of the wheat gliadin gene, of the wheat glutelin gene, of the maize zein gene, of the oat glutelin gene, of the sorghum kasirin gene or of the rye secalin gene, which are described in WO99/16890.

Further particularly preferred promoters are those which ensure expression in tissues or plant parts in which, for example, the biosynthesis of fatty acids, oils and lipids and their precursors takes place. Particular mention should be made of promoters which ensure seed-specific expression. Mention should be made of the oilseed rape napin gene promoter (U.S. Pat. No. 5,608,152), the *Vicia faba* USP promoter (USP=unknown seed protein, Baeumlein et al., Mol Gen Genet, 1991, 225 (3): 459-67), of the *Arabidopsis* oleosin gene (WO98/45461), of the phaseolin promoter (U.S. Pat. No. 5,504,200) or of the legumin B4 gene promoter (LeB4; Baeumlein et al., 1992, Plant Journal, 2 (2): 233-9). Mention should furthermore be made of promoters such as that of the barley lpt2 or lpt1 gene (WO95/15389 and WO95/23230), which ensure seed-specific expression in monocots.

The expression cassette (=gene construct, nucleic acid construct) may, as described above, comprise other genes which are to be introduced into the organisms. These genes may be regulated separately or be in the same regulatory region as the Δ6-desaturase gene. These genes are advantageously further biosynthesis genes, advantageously of fatty acid biosynthesis, which allow increased synthesis. Examples which may be mentioned are the genes for Δ15-, Δ12-, Δ9-, Δ5- and Δ4-desaturase, the various hydroxylases, the acyl ACP thioesterases, β-ketoacyl synthases or β-ketoacyl reductases. It is advantageous to use the desaturase genes in the nucleic acid construct.

In principle, it is possible for all natural promoters with their regulatory sequences like those mentioned above to be used for the expression cassette according to the invention and the process according to the invention, as described below. It is also possible and advantageous to use synthetic promoters.

It is possible to manipulate various DNA fragments in order to obtain a nucleotide sequence which is expediently read in the correct direction and which is equipped with a correct reading frame. To link the DNA fragments (=nucleic acids according to the invention) to each other adapters or linkers may be attached to the fragments.

Expediently, the promoter and terminator regions may be provided, in the direction of transcription, with a linker or polylinker comprising one or more restriction sites for insertion of this sequence. As a rule, the linker has 1 to 10, in most cases 1 to 8, preferably 2 to 6, restriction sites. The size of the linker within the regulatory region is generally less than 100 bp, frequently less than 60 bp, but at least 5 bp. The promoter can be either native, or homologous, or else foreign, or heterologous, in relation to the host organism, for example the host plant. The expression cassette comprises in the 5'-3'-direction of transcription the promoter, a DNA sequence encoding a Δ6-desaturase gene used in the process according to the invention, and a region for transcriptional termination. Various termination regions can be exchanged for each other as desired.

It is furthermore possible to employ manipulations which provide suitable restriction cleavage sites or which eliminate excess DNA or restriction cleavage sites. Where insertions, deletions or substitutions such as, for example, transitions and transversions, are suitable, in vitro mutagenesis, primer repair, restriction or ligation may be used. In suitable manipulations such as, for example, restriction, chewing back or filling in overhangs for blunt ends, complementary ends of the fragments may be provided for ligation.

Attachment of the specific ER retention signals SEKDEL (SEQ ID NO: 3) (Schouten, A. et al., Plant Mol. Biol. (1996), 781-792), may, inter alia, be of importance for advantageous high-level expression, thus tripling to quadrupling the average level of expression. It is also possible to employ other retention signals which occur naturally with plant and animal proteins localized in the ER for constructing the cassette.

Preferred polyadenylation signals are plant polyadenylation signals, preferably those which correspond essentially to T-DNA-polyadenylation signals from *Agrobacterium tumefaciens*, in particular gene 3 of the T-DNA (octopin synthase) of the Ti-plasmids pTiACH5 (Gielen et al., EMBO J. 3 (1984), 835 et seq.) or corresponding functional equivalents.

An expression cassette is generated by fusing a suitable promoter to a suitable Δ6-desaturase DNA sequence and to a polyadenylation signal by conventional recombination and cloning techniques as described, for example, in T. Maniatis, E. F. Fritsch and J. Sambrook, Molecular Cloning: A Laboratory Manual, Cold Spring Harbor Laboratory, Cold Spring Harbor, N.Y. (1989), T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley-Interscience (1987).

The DNA sequence encoding a *Physcomitrella patens* Δ6-desaturase comprises all sequence characteristics which are necessary to achieve correct localization for the site of fatty acid, lipid or oil biosynthesis. No further targeting sequences are therefore necessary per se. However, such localization may be desirable and advantageous and can therefore be modified or enhanced artificially, so that such fusion constructs are also a preferred advantageous embodiment of the invention.

Particularly preferred sequences are those which ensure targeting into plastids. Under certain circumstances, targeting into other compartments (see review in: Kermode, Crit. Rev. Plant Sci. 15, 4 (1996), 285-423) for example into the vacuole, into the mitochondrion, into the endoplasmic reticulum (ER), peroxisomes, lipid bodies or, owing to the absence of suitable operative sequences, remaining in the compartment of formation, namely the cytosol, may also be desirable.

The nucleic acid sequences encoding Δ6-desaturase genes are advantageously cloned together with at least one reporter gene into an expression cassette which is introduced into the organism via a vector or directly into the genome. This reporter gene should make easy detection possible by a growth, fluorescence, chemo- or bioluminescence or resistance assay or by a photometric measurement. Examples of reporter genes are genes for resistance to antibiotics or herbicides, hydrolase genes, fluorescence protein genes, bioluminescence genes, sugar or nucleotide metabolism genes or biosynthesis genes such as the Ura3 gene, the Ilv2 gene, the luciferase gene, the f-galactosidase gene, the gfp gene, the 2-desoxyglucose-β-phosphate phosphatase gene, the β-glucuronidase gene, β-lactamase gene, the neomycin phosphotransferase gene, the hygromycin phosphotransferase gene or the BASTA (=glufosinate resistance) gene. These genes make it possible easily to measure and quantify the transcriptional activity and thus gene expression. It is thus possible to identify sites in the genome which show differences in productivity.

In a preferred embodiment, an expression cassette comprises upstream, i.e. at the 5' end of the coding sequence, a promoter and downstream i.e. at the 3' end, a polyadenylation signal, if appropriate, further regulatory elements which are operatively linked to the interposed coding sequence for the Δ6-desaturase DNA sequence. Operative linkage is to be understood as meaning the sequential arrangement of promoter, coding sequence, terminator and, if appropriate, other regulatory elements in such a manner that each of the regulatory elements can carry out its function as intended in the expression of the coding sequence. The sequences preferred for operative linkage are targeting sequences for ensuring subcellular localization in plastids. However, targeting sequences to ensure subcellular localization in the mitochondrion, in the endoplasmatic reticulum (ER), in the nucleus, in oleoplasts or other compartments may also be employed if required, as well as translation enhancers such as the tobacco mosaic virus 5' leader sequence (Gallie et al., Nucl. Acids Res. 15 (1987), 8693-8711).

An expression cassette can comprise, for example, a constitutive promoter (preferably the USP or napin promoter), the gene to be expressed and the ER retention signal. The ER retention signal which is preferably used is the amino acid sequence KDEL (lysine, aspartic acid, glutamic acid, leucine) (SEQ ID NO: 13).

For expression in a prokaryotic or eukaryotic host organism, for example a microorganism such as a fungus or plant, the expression cassette is advantageously inserted into a vector such as, for example, a plasmid, a phage or other DNA which allows optimal expression of the genes in the host organism. Examples of suitable plasmids are in *E. coli* pLG338, pACYC184, pBR series such as, for example, pBR322, pUC series such as pUC18 or pUC19, M113 mp series, pKC30, pRep4, pHS1, pHS2, pPLc236, pMBL24, pLG200, pUR290, pIN-III$^{113}$-B1, λgtll or pBdCI, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, other advantageous fungal vectors being described by Romanos, M. A. et al., [(1992) "Foreign gene expression in yeast: a review", Yeast 8: 423-488] and by van den Hondel, C. A. M. J. J. et al. [(1991) "Heterologous gene expression in filamentous fungi] and in More Gene Manipulations in Fungi [J. W. Bennet & L. L. Lasure, eds., pp. 396-428: Academic Press: San Diego] and in "Gene transfer systems and vector development for filamentous fungi" [van den Hondel, C. A. M. J. J. & Punt, P. J. (1991) in: Applied-Molecular Genetics of Fungi, Peberdy, J. F. et al., eds., pp. 1-28, Cambridge University Press: Cambridge]. Advantageous yeast vectors are, for example 2 μM, pAG-1, YEp6, YEp13 or pEMBLYe23. Examples of algal or plant promoters are pLGV23, pGHlac⁺, pBIN19, pAK2004, pVKH or pDH51 (see Schmidt, R. and Willmitzer, L., 1988). The abovementioned vectors or derivatives of the abovementioned vectors constitute a small selection of plasmids which are possible. Further plasmids are well known to the skilled worker and can be found, for example, in the book Cloning Vectors (Eds. Pouwels P. H. et al. Elsevier, Amsterdam-New York-Oxford, 1985, ISBN 0 444 904018). Suitable plant vectors are described, inter alia, in "Methods in Plant Molecular Biology and Biotechnology" (CRC Press), Chap. 6/7, pp. 71-119. Advantageous vectors are shuttle vectors or binary vectors, which replicate in *E. coli* and *Agrobacterium*.

Apart from plasmids, vectors also mean all other vectors known to the skilled worker, such as, for example, phages, viruses such as SV40, CMV, baculovirus, adenovirus, transposons, IS elements, phasmids, phagemids, cosmids, linear or cyclic DNA. These vectors are capable of autonomous replication or chromosomal replication in the host organism; chromosomal replication is preferred.

In a further embodiment of the vector, the expression cassette according to the invention can also advantageously be introduced into the organisms in the form of a linear DNA and integrated into the genome of the host organism by heterologous or homologous recombination. This linear DNA may consist of a linearized plasmid or else only of the expression cassette as vector or the nucleic acid sequences according to the invention.

In a further advantageous embodiment, the nucleic acid sequence according to the invention can also be introduced alone into an organism.

If, in addition to the nucleic acid sequence according to the invention, further genes are to be introduced into the organism, it is possible to introduce them all together with a reporter gene in a single vector or each individual gene with a reporter gene in one vector in each case, or several genes together in various vectors, into the organism, in which case the various vectors can be introduced simultaneously or successively.

The vector advantageously comprises at least one copy of the nucleic acid sequences encoding a Δ6-desaturase, and/or of the expression cassette.

By way of example, the plant expression cassette can be incorporated into the transformation vector pRT ((a) Toepfer et al., 1993, Methods Enzymol., 217: 66-78; (b) Toepfer et al. 1987, Nucl. Acids. Res. 15: 5890 et seq.).

As an alternative, a recombinant vector (=expression vector) can also be transcribed and translated in vitro, for example by using the T7 promoter and T7 RNA polymerase.

Expression vectors used in prokaryotes frequently make use of inducible systems with and without fusion proteins or fusion oligopeptides, it being possible for these fusions to take place both at the N terminus and at the C terminus or other domains of a protein which can be used. As a rule, such fusion vectors are intended to: i.) increase the RNA expression rate, ii.) increase the protein synthesis rate which can be achieved, iii.) increase the solubility of a protein, or iv.) simplify purification by a binding sequence which can be used for affinity chromatography. Proteolytic cleavage sites are frequently also introduced by fusion proteins, enabling purification to include elimination of part of the fusion protein as well. Such recognition sequences for proteases recognize, for example, factor Xa, thrombin and enterokinase.

Typical advantageous fusion and expression vectors are pGEX [Pharmacia Biotech Inc; Smith, D. B. and Johnson, K. S. (1988) *Gene* 67: 31-40], pMAL (New England Biolabs, Beverly, Mass.) and pRIT5 (Pharmacia, Piscataway, N.J.), which comprises glutathione S transferase (GST), maltose binding protein, or protein A.

Further examples of *E. coli* expression vectors are pTrc [Amann et al., (1988) *Gene* 69:301-315] and pET vectors [Studier et al., Gene Expression Technology: Methods in Enzymology 185, Academic Press, San Diego, Calif. (1990) 60-89; Stratagene, Amsterdam, The Netherlands].

Further advantageous vectors for use in yeasts are pYepSec1 (Baldari, et al., (1987) *Embo J.* 6:229-234), pMFa (Kurjan and Herskowitz, (1982) *Cell* 30:933-943), pJRY88 (Schultz et al., (1987) *Gene* 54:113-123), and pYES derivatives (Invitrogen Corporation, San Diego, Calif.). Vectors for use in filamentous fungi are described in: van den Hondel, C. A. M. J. J. & Punt, P. J. (1991) "Gene transfer systems and vector development for filamentous fungi, in: Applied Molecular Genetics of Fungi, J. F. Peberdy, et al., eds., pp. 1-28, Cambridge University Press: Cambridge.

As an alternative, insect cell expression vectors may also be used advantageously, for example for the expression in Sf 9 cells. Examples of these are the vectors of the pAc series (Smith et al. (1983) *Mol. Cell Biol.* 3:2156-2165) and of the pVL series (Lucklow and Summers (1989) *Virology* 170:31-39).

Moreover, plant cells or algal cells may advantageously be used for gene expression. Examples of plant expression vectors are found in Becker, D., et al. (1992) "New plant binary vectors with selectable markers located proximal to the left border", *Plant Mol. Biol.* 20: 1195-1197 or in Bevan, M. W. (1984) "Binary *Agrobacterium* vectors for plant transformation", *Nucl. Acid. Res.* 12: 8711-8721.

Moreover, the nucleic acid sequences encoding Δ6-desaturase may also be expressed in mammalian cells. Examples of suitable expression vectors are pCDM8 and pMT2PC, mentioned in: Seed, B. (1987) *Nature* 329:840 or Kaufman et al. (1987) *EMBO J.* 6: 187-195). Promoters preferably to be used in such cases are of viral origin, such as, for example, promoters of polyoma virus, adenovirus 2, cytomegalovirus or simian virus 40. Further prokaryotic and eukaryotic expression systems are mentioned in Chapters 16 and 17 in Sambrook et al., *Molecular Cloning: A Laboratory Manual. 2nd ed., Cold Spring Harbor Laboratory*, Cold Spring Harbor Laboratory Press, Cold Spring Harbor, N.Y., 1989.

The introduction of the nucleic acids according to the invention, of the expression cassette or of the vector into organisms, for example into plants, can in principle take place by all methods known to the skilled worker.

The skilled worker can find suitable methods for microorganisms in the textbooks by Sambrook, J. et al. (1989) Molecular cloning: A laboratory manual, Cold Spring Harbor Laboratory Press, by F. M. Ausubel et al. (1994) Current protocols in molecular biology, John Wiley and Sons, by D. M. Glover et al., DNA Cloning Vol. 1, (1995), IRL Press (ISBN 019-963476-9), by Kaiser et al. (1994) Methods in Yeast Genetics, Cold Spring Habor Laboratory Press or Guthrie et al, Guide to Yeast Genetics and Molecular Biology, Methods in Enzymology, 1994, Academic Press.

The transfer of foreign genes into the genome of a plant is termed transformation. Use is made here of the above-described methods for the transformation and regeneration of plants from plant tissues or plant cells for transient or stable transformation. Suitable methods are protoplast transformation by polyethylene glycol-induced DNA uptake, the biolistic method with the gene cannon, the particle bombardment method, electroporation, incubation of dry embryos in DNA-containing solution, microinjection and *agrobacterium*-mediated gene transfer. The methods mentioned are described, for example, by B. Jenes et al., Techniques for Gene Transfer, in: Transgenic Plants, Vol. 1, Engineering and Utilization, edited by S. D. Kung and R. Wu, Academic Press (1993) 128-143 and Potrykus, Annu. Rev. Plant Physiol. Plant Molec. Biol. 42 (1991) 205-225). The construct to be expressed advantageously clones into a vector suitable for transforming *Agrobacterium tumefaciens*, for example pBin19 (Bevan et al., Nucl. Acids Res. 12 (1984) 8711). *Agrobacteria* transformed with such a vector can then be used in the known manner for transforming plants, in particular crop plants such as, for example tobacco plants, for example by bathing scarified leaves or leaf sections in an agrobacterial solution and subsequently growing them in suitable media. The transformation of plants with *Agrobacterium tumefaciens* is described, for example, by Höfgen and Willmitzer in Nucl. Acid Res. (1988) 16, 9877 or is known, inter alia, from F. F. White, Vectors for Gene Transfer in Higher Plants; in Transgenic Plants, Vol. 1, Engineering and Utilization, edited by S. D. Kung and R. Wu, Academic Press, 1993, pp. 15-38.

*Agrobacteria* transformed with an expression vector as described above can also be used in a known manner for transforming plants such as test plants such as *Arabidopsis* or crop plants such as cereals, maize, oats, rye, barley, wheat, soybean, rice, cotton, sugarbeet, canola, triticale, sunflower, flax, hemp, potato, tobacco, tomato, coffee, cacao, tea, carrot, *capsicum*, oilseed rape, tapioca, carcaba, arrowroot, tagetes, alfalfa, lettuce and the various tree, nut and grapevine species, in particular oil-containing crop plants such as soybean, peanut, castor, borrage, linseed, sunflower, canola, cotton, flax, oilseed rape, coconut, oilpalm, safflower (*Carthamus tinctorius*) or cacao bean, for example by bathing scarified leaves or leaf sections in an agrobacterial solution and subsequently growing them in suitable media.

The genetically modified plant cells can be regenerated by all methods known to the skilled worker. Suitable methods can be found in the abovementioned publications by S. D. Kung and R. Wu, Potrykus or Höfgen and Willmitzer.

Organisms or host organisms for the nucleic acids used [lacuna] processes according to the invention, the expression cassette used or the vector used are, in principle and advantageously, all organisms which are capable of synthesizing fatty acids, specifically unsaturated fatty acids, or which are suitable for the expression of recombinant genes. Examples which may be mentioned are plants such as *Arabidopsis*, *Asteraceae* such as *calendula*, or crop plants such as soybean, peanut, castor, sunflower, maize, cotton, flax, oilseed rape, coconut, oilpalm, safflower (*Carthamus tinctorius*) or cacao bean, microorganisms such as fungi, for example the genus *Mortierella*, *Saprolegnia* or *Pythium*, bacteria such as the genus *Escherichia*, cyanobacteria, ciliates, thraustochytria or schizichytria, algae or protozoa such as dinoflagellates such as Crypthecodinium. Preferred organisms are those which are capable of naturally synthesizing oils in substantial amounts, such as fungi of the genera *Mortierella* or *Pythium*, such as *Mortierella alpina* and *Pythium insidiosum*, or plants such as soybean, oilseed rape, coconut, oilpalm, safflower, castor, *calendula*, peanut, cacao bean or sunflower, with soybean, oilseed rape, sunflower, castor, *Mortierella* or *Pythium* being especially preferred. In principle, transgenic animals, for example *C. elegans*, are also suitable as host organisms.

Host cells which can be used are also mentioned in: Goeddel, *Gene Expression Technology Methods in Enzymology* 185, Academic Press, San Diego, Calif. (1990).

Expression strands which can be used, for example those which have a lower protease activity, are described in: Gottesman, S., *Gene Expression Technology: Methods in Enzymology* 185, Academic Press, San Diego, Calif. (1990) 119-128.

Depending on the choice of the promoter, expression of the Δ6-desaturase gene may take place specifically in the leaves, in the seeds, the tubers or other parts of the plant. The present invention furthermore relates to such transgenic plants which overproduce fatty acids, oils or lipids, and to their propagation material and their plant cells, tissue or plant parts. A preferred subject according to the invention is transgenic plants of, for example, crop plants such as maize, oats, rye, wheat, barley, rice, soybean, sugarbeet, canola, triticale, sunflower, flax, hemp, tobacco, tomato, coffee, cacao, tea, carrot, *capsicum*, oilseed rape, tapioca, carcaba, arrowroot, tagetes, alfalfa, lettuce and the various tree, nut and grapevine species, potatoes, in particular oil-containing crop plants such as soybean, peanut, castor, borrage, linseed, sunflower, canola, cotton, flax, oilseed rape, coconut, oilpalm, safflower (*Carthamus tinctorius*) or cacao bean, laboratory plants such as *Arabidopsis*, or other plants such as mosses or algae comprising a functional nucleic acid sequence according to the invention or a functional expression cassette. Functional in this context means that an enzymatically active enzyme is formed.

The expression cassette or the nucleic acid sequences according to the invention comprising a Δ6-desaturase gene sequence can additionally also be used for the transformation of the organisms which have been mentioned above by way of example, such as bacteria, cyanobacteria, filamentous fungi, ciliates, animals or algae, with the aim of increasing the content in fatty acids, oils or lipids of Δ6-double bonds. Preferred transgenic organisms are bacteria, cyanobacteria, filamentous fungi or algae.

Transgenic organisms are to be understood as meaning organisms which comprise a foreign nucleic acid derived from another organism which encodes a Δ6-desaturase used in the process according to the invention. Transgenic organisms are also to be understood as meaning organisms which comprise a nucleic acid which is derived from the same organism and encodes a Δ6-desaturase, this nucleic acid being present as an additional gene copy or not being present in the natural nucleic acid environment of the Δ6-desaturase gene. Transgenic organisms are also organisms in which the natural 3'- and/or 5'-region of the Δ6-desaturase gene has been modified over the initial organisms by targeted, recombinant modifications. Preferred transgenic organisms are those into which a foreign DNA has been introduced. Especially preferred are transgenic plants into which a foreign DNA has been introduced. Transgenic plants are to be understood as meaning individual plant cells and their cultures, such as, for example, callus cultures on solid media or in liquid culture, the plant parts and intact plants.

The invention furthermore relates to transgenic organisms selected from the group of the plants, fungi, ciliates, algae, bacteria, cyanobacteria or animals, preferably transgenic plants or algae, comprising at least one isolated nucleic acid sequence encoding a polypeptide with Δ6-desaturase activity, selected from the group consisting of:

a) a nucleic acid sequence having the sequence shown in SEQ ID NO: 1,
b) nucleic acid sequences which, as a result of the degeneracy of the genetic code, are derived from the sequence shown in SEQ ID NO: 1,
c) derivatives of the nucleic acid sequence shown in SEQ ID NO: 1 which encode polypeptides with the amino acid sequences shown in SEQ ID NO: 2 and have at least 50% homology at the amino acid level without substantially reducing the enzymatic action of the polypeptides.

Increasing the content of fatty acids, oils or lipids with Δ6-double bonds means for the purposes of the present invention for example the artificially acquired ability of an increased biosynthesis performance by functionally overexpressing the Δ6-desaturase gene in the organisms according to the invention, advantageously in the transgenic plants according to the invention, in relation to the nonrecombinant initial plants, at least for the duration of at least one plant generation.

The biosynthesis site of fatty acids, oils or lipids, for example, is generally the seed or cell layers of the seed, so that seed-specific expression of the Δ6-desaturase gene is meaningful. However, it is obvious that the biosynthesis of fatty acids, oils or lipids need not be restricted to the seed tissue, but may also take place in a tissue-specific manner in all remaining parts of the plant, for example in epidermis cells or in the tubers.

In addition, constitutive expression of the exogenous Δ6-desaturase gene is advantageous. However, inducible expression may also be desirable.

The efficacy of expression of the Δ6-desaturase gene can be determined for example in vitro by shoot meristem propagation. In addition, an expression of the Δ6-desaturase gene whose type and level has been modified, and its effect on fatty acid, oil or lipid biosynthetic activity can be tested in glasshouse experiments on test plants.

The invention relates to transgenic plants as described above, transformed with a nucleic acid sequence encoding a Δ6-desaturase, a vector or an expression cassette comprising a Δ6-desaturase gene sequence or DNA sequences hydribizing herewith, and to transgenic cells, tissue, parts and propagation material of such plants. Especially preferred in this context are transgenic crop plants as described above.

Plants for the purposes of the invention are monocots and dicots or algae.

The invention furthermore relates to:
the use of a Δ6-desaturase DNA gene sequence with the sequence stated in SEQ ID NO:1 or DNA sequences hybridizing herewith for the generation of fungi, bacteria, animals or plants, preferably plants, with an increased content of fatty acids, oils or lipids with Δ6-double bonds by expressing this Δ6-desaturase DNA sequence in plants.
the use of the proteins with the sequences SEQ ID NO: 2 for the preparation of unsaturated fatty acids in plants, fungi, bacteria or animals, preferably plants.

The invention is illustrated in greater detail by the examples which follow:

EXAMPLES

Example 1

General Cloning and Culture Methods

The cloning methods such as, for example, restriction cleavages, agarose gel electrophoresis, purification of DNA fragments, transfer of nucleic acids to nitrocellulose and nylon membranes, linking of DNA-fragments, transformation of *Escherichia coli* cells, cultivation of organisms, and the sequence analysis of recombinant DNA, were carried out as described by Sambrook et al. (1989) (Cold Spring Harbor Laboratory Press: ISBN 0-87969-309-6). The protonema of *Physcomitrella patens* (=*P. patens*) was cultured in liquid medium as described by Reski et al. (Mol. Gen. Genet., 244, 1994: 352-359).

Example 2

Recombinant DNA Sequence Analysis

Recombinant DNA molecules were sequenced using an ABI laser fluorescence DNA sequencer by the method of Sanger (Sanger et al. (1977) Proc. Natl. Acad. Sci. USA 74, 5463-5467). Fragments resulting from a polymerase chain reaction were sequenced and checked to avoid polymerase errors in constructs to be expressed.

Example 3

Analysis of Lipid from the *P. patens* Protonema and from Yeast Cells

The lipids were extracted from the *P. patens* Protonema or from yeast cells using chloroform/methanol as described by Siebertz et al. (Eur. J. Biochem., 101, 1979: 429-438) and purified with diethyl ether by thin-layer chromatography (=TLC). The fatty acids obtained were transmethylated to give the corresponding methyl esters and analyzed by gas chromatography (=GC). The various methyl esters were identified using corresponding standards. Corresponding fatty acid pyrrolidides were obtained, and identified by GC-MS, as described by Anderson et al. (Lipids, 9, 1974: 185-190).

Example 4

Functional Expression of the *P. patens* Δ6-Desaturase cDNA in Yeasts

The expression experiments in yeasts were carried out with PPDES6 cDNA. Knock-out experiments had shown (data and experimental procedure not shown or described) that the knock-out effect leads to a loss of $20:3^{11,14,17}$-, $20:4^{5,8,11,14}$-, $20:4^{5,11,14,17}$- and $20:5^{5,8,11,14,17}$-fatty acids. The $18:2^{9,12}$- and $18:3^{9,12,15}$-fatty acids increase simultaneously. For expression in yeast, the PPDES6 cDNA was subcloned into the yeast expression vector pYES2 (Invitrogen). The vector obtained was named pYESdelta6. Yeast cultures transformed with pYES2 (control) and pYESdelta6 (Δ6-desaturase cDNA) were cultured on uracil drop-out medium supplemented with 2% raffinose and 1% Tergitol NP-40 (for stabilizing the fatty acids). For expression, the cells were cultured with galactose (final concentration 2%) up to an optical density (=OD) of 0.5 and 600 nm. In feeding experiments, fatty acids were solubilized in 5% Tergitol and added at a final concentration of 0.0003%. The results of expression can be found in Table I. The synthesis of fatty acids with a double bond at position 6 is only possible in the presence of the expression construct with the Δ6-desaturase cDNA. This Δ6-desaturase enzyme had a greater activity in relation to fatty acids which already contain a double bond at position 9 or 12 (relative to carbon atom in the chain). The fatty acid methyl esters of all of the yeast lipids were analyzed by GC. The individual fatty acids synthesized are shown in the table in mol % of the overall fatty acids.

Table I

Fatty acid composition in transformed yeasts in relation to the control
Overall fatty acids (%)

| Fatty acids | pYES2 | | pYESdelta6 | |
|---|---|---|---|---|
| | | | $+18:2^{9,12}$ | $+18:3^{9,12,15}$ |
| 16:0 | 16.4 | 16.1 | 23.8 | 25.8 |
| $16:1^9$ | 54.0 | 55.5 | 38.1 | 31.4 |
| $16:2^{6,9}$ | — | 4.2 | 1.7 | — |
| 18:0 | 3.2 | 2.4 | 4.0 | — |
| $18:1^9$ | 24.9 | 19.7 | 19.1 | 19.2 |
| $18:2^{6,9}$ | — | 0.6 | 0.2 | — |
| $18:2^{9,12}$ | — | — | 8.5 | — |
| $18:3^{6,9,12}$ | — | — | 4.0 | — |
| $18:3^{9,12,15}$ | — | — | — | 11.7 |
| $18:4^{6,9,12,15}$ | — | — | — | 3.0 |

Example 5

Transformation of *P. patens*

The polyethylene glycol-mediated direct DNA transformation of protoplasts was carried out as described by Schafer et al. (Mol. Gen. Genet., 226, 1991: 418-424). The transformants were selected on G418-containing medium (Girke et al., The Plant Journal, 15, 1998: 39-48).

Example 6

Isolation of Δ6-Desaturase cDNA and Genomic Clones of *P. patens*

Eventually fragments of a Δ6-desaturase gene were cloned with the aid of a PCR reaction with the following degenerate oligonucleotides as primers:

```
A:  TGGTGGAA(A/G)TGGA(C/A)ICA(T/C)AA
    and

B:  GG(A/G)AA(A/C/G/T)A(A/G)(G/A)TG(G/A)TG(C/T)TC]
``` and the following temperature program:
94° C., 3 min; [94° C., 20 sec; 45° C., 30 sec; 72° C., 1 min], 30 cycles; 72° C., 5 min. For cloning, poly(A)RNA was isolated from 12-day-old *P. patens* Protonema cultures. The above-described PCR was carried out with this poly(A)RNA. Fragments of the expected fragment length (500 to 600 bp) were cloned into pUC18 and sequenced. The deduced amino acid sequence of a PCR fragment showed similarities with known Δ6-desaturases. Since it was known that *P. patens* has a Δ6-desaturase, it was assumed that this clone encodes part of a Δ6-desaturase.

A complete cDNA clone (=PPDES6 cDNA) was isolated from *P. patens* cDNA library of 12-day-old Protonemata with the aid of the PCR fragment specified above. The nucleotide sequence is shown in SEQ ID NO:1. The deduced amino acid sequence can be seen from SEQ ID NO:2. The corresponding genomic sequence (=PPDES6 gene) was isolated with the aid of the PCR and the following oligonucleotides as primers:

```
                                          (SEQ ID NO: 6)
    C: CCGAGTCGCGGATCAGCC (SEQ ID NO: 7)
    D: CAGTACATTCGGTCATTCACC:
```

Table II shows the results of the comparison between the novel *P. patens* Δ6-desaturase over the entire nucleic acid sequence with the following, known Δ6-desaturase: *Borago officinalis* (U79010), *Synechocystis* sp (L11421), *Spirulina platensis* (X87094), *Caenorhabiditis elegans* (AF031477), *Mortierella alpina* (WO 98/46764), *Homo sapiens* (Cho et al., J. Biol. Chem., 274, 1999: 471-477), *Rattus norvegicus* (AB021980) and *Mus musculus* (Cho et al., J. Biol. Chem., 274, 1999: 471-477). The analysis was carried out with the Gap Program (GCG Package, Version 9.1) and the following analysis parameters: scoring matrix, blosum62, gap creation penalty, 12; gap extension penalty, 4. The results show the particular identity or similarity [ ] in percent (%) in relation with the *P. patens* sequence.

Table II

Sequence comparison between *P. patens* Δ6-desaturase and other Δ6-desaturases

| Sequence | Amino acid sequence identity [similarity] (%) |
|---|---|
| *Borago officinalis* | 31 [38] |
| *Synechocystis* sp. | 21 [29] |
| *Spirulina platensis* | 20 [29] |
| *Caenorhabiditis elegans* | 35 [43] |
| *Mortierella alpina* | 39 [47] |
| *Homo sapiens* | 27 [38] |
| *Rattus norvegicus* | 28 [39] |
| *Mus musculus* | 29 [39] |

Example 7

Cloning the *Physcomitrella patens* Δ6-desaturase

The genomic Δ6-acyllipid desaturase from *Physcomitrella patens* was modified, isolated and used in the process according to the invention on the basis of the published sequence (Girke et al., Plant J., 15, 1998: 39-48) using a polymerase chain reaction and cloning. To this end, a desaturase fragment was first isolated by means of polymerase chain reaction using two gene-specific primers, and inserted into the desaturase gene described in Girke et al. (see above).

```
                                          (SEQ ID NO: 8)
    Primer TG5: 5'-ccgctcgagcgaggttgttgtggagcggc
    and (SEQ ID NO: 9)
    Primer TG3: 5'-ctgaaatagtcttgctcc-3'
``` were first used for amplifying a gene fragment by means of polymerase chain reaction (30 cycles, 30 sec. at 94° C., 30 sec. at 50° C., 60 sec. at 72° C., post-incubation for 10 minutes at 72° C., in a Perkin Elmer thermocycler).

a) Cloning an expression plasmid expressing Δ6-desaturase under the control of the 35S CaMV [sic] promoter:

An XhoI cleavage site was introduced into the fragment by the primer TG5. An XhoI/Eco47III fragment was obtained by restriction and transposed into the PPDES6 gene sequence described in Girke et al. following analogous restriction with XhoI/Eco47III. The construct was named pZK. The insert of pZK was cloned into the XhoI/SmaI cleavage site of pRT99/35S as XhoI/HindIII fragment after filling up the HindIII cleavage site with nucleotides by treatment with the Klenow fragment of DNA polymerase I. The resulting plasmid pSK contains the 35S promoter [cauliflower mosaic virus, Franck et al. (1980) Cell 21, 285], the moss Δ6-desaturase and the 35S terminator in the vector pRT.

b) Construction of an expression construct under the control of the napin promoter:

The resulting promoter desaturase fragment with terminator was cloned into the vector pJH3 by cleaving the plasmid pSK with XhoI, treatment with T4 DNA polymerase and PstI restriction. To this end, the vector BamHI was cleaved, the overhangs were filled up with Klenow enzyme, and this was followed by cutting with PstI. Ligation of the desaturase terminator fragment into the vector gave rise to the plasmid pJH7, which contains a napin promoter (Scofield et al., 1987, J. Biol. Chem. 262, 12202-8). The expression cassette of pJH7 was cleaved with Bsp120I and NotI and cloned into the binary vector pRE. This gave rise to the plasmid pRE-Ppdes6.

In a PCR reaction, the *P. patens* Δ6-desaturase cDNA according to the invention was used as template. With the aid of the oligonucleotides stated hereinbelow, a BamHI restriction cleavage site was introduced before the start codon and three adenine nucleotides were introduced into the Δ6-desaturase cDNA as consensus translation sequence for eukaryotes. A 1512 base pair fragment of the Δ6-desaturase was amplified and sequenced.

```
                                          (SEQ ID NO: 10)
Pp-d6Des1: 5'-CC GGTACC aaaatggtattcgcgggcggtg-3'

(SEQ ID NO: 11)
Pp-d6Des2: 3'-CC GGTACC ttaactggtggtagcatgct-3'
```

The reaction mixtures contained approximately 1 ng/μl template DNA, 0.5 μm of the oligonucleotides and, 200 μm deoxy-nucleotides (Pharmacia), 50 mM KCl, 10 mM Tris-HCl (pH 8.3 at 25° C., 1.5 mM MgCl$_2$) and 0.02 U/μl Pwo polymerase (Boehringer Mannheim) and are incubated in a Perkin Elmer PCR machine with the following temperature program:

Annealing temperature: 50° C., sec
Denaturation temperature: 95° C., sec
Elongation temperature: 72° C., 90 sec
Number of cycles: 30 c) Construction of an expression construct under the control of the USP promoter:

The resulting fragment of approx. 1.5 kB base pairs was ligated into the vector pBluescript SK—(Stratagene) which had been cleaved with EcoRV and was available for further clonings as BamHI fragment.

For the transformation of plants, a further transformation vector based on pBin-USP was generated, and this transformation vector contains the Δ6-desaturase BaMHI fragment. pBin-USP is a derivative of plasmid pBin19. pBinUSP originated from pBin19, by inserting an USP promoter into pBin19 [Bevan et al. (1980) Nucl. Acids Res. 12, 8711] as EcoRI-BamHI fragment. The polyadenylation signal is that of gene 3 of the T-DNA of the Ti-plasmid pTiACH5 (Gielen et al., (1984) EMBO J. 3, 835), where the nucleotides 11749-11939 were isolated as PvuII-HindIII fragment and, after the addition of SphI-linkers, cloned at the PvuII cleavage site between the SpHI-HindIII cleavage site of the vector. The USP promoter corresponds to the nucleotides 1-684 (Genbank Accession X56240), where part of the noncoding region of the USP gene was obtained in the promoter. The promoter fragment which is 684 base pairs in size was amplified with the aid of commercially available T7 standard primer (Stratagene) and with the aid of a synthesized primer via a PCR reaction using standard methods (primer sequence: 5'-GTCGACCCGCGGAC-TAGTGGGCCCTCTAGACCCGGGGGATCC GGATCTGCTGGCTATGAA-3'). The PCR fragment was subsequently cut with EcoRI/SalI and inserted into the vector pBin19 with OCS terminator. This gave rise to the plasmid named pBinUSP.

d) Construction of an expression construct under the control of the *Beta vulgaris* vATPase C1 promoter:

A construct using the v-ATPase-c1 promoter was generated analogously to the expression plasmid with the USP promoter. The promoter was cloned into the plasmid pBin19 with OCS terminator as an EcoRI/KpnI fragment and the *P. patens* Δ6-desaturase gene was inserted between promoter and terminator via BaMHI. The promoter corresponds to a *Beta vulgaris* 1153 base pair fragment (Plant Mol Biol, 1999, 39:463-475).

The construct was employed for the transformation of *Arabidopsis thaliana* and oilseed rape plants.

Example 8

Generation of Transgenic Oilseed Rape Plants (Modified According to Moloney et al., 1992, Plant Cell Reports, 8:238-242)

To generate transgenic oilseed rape plants, binary vectors were made use of in *Agrobacterium tumefaciens* C58C1: pGV2260 or *Escherichia coli* (Deblaere et al, 1984, Nucl. Acids. Res. 13, 4777-4788). To transform oilseed rape plants (var. *Drakkar*, NPZ Norddeutsche Pflanzenzucht, Hohenlieth, Germany), a 1:50 dilution of an overnight culture of a positively transformed agrobacterial colony grown in Murashige-Skoog Medium (Murashige and Skoog 1962 Physiol. Plant. 15, 473) supplemented with 3% of sucrose (3MS medium) was used. Petioles or hypocotyledons [sic] of freshly germinated sterile oilseed rape plants (in each case approx. 1 cm²) were incubated for 5-10 minutes in a Petri dish together with a 1:50 agrobacterial dilution. This was followed by 3 days' incubation in the dark at 25° C. on 3MS medium with 0.8% Bacto agar. After 3 days, the culture was continued under 16 hours light/8 hours dark, and continued in a weekly rhythm on MS medium supplemented with 500 mg/l Claforan (cefotaxime sodium), 50 mg/l kanamycin, 20 μM benzylaminopurine (BAP) and 1.6 g/l glucose. Growing shoots were transferred to MS medium supplemented with sucrose, 250 mg/l Claforan and 0.8% Bacto agar. If no roots have formed after three weeks, 2-indolebutyric acid was added to the medium as growth hormone for rooting.

Regenerated shoots were obtained on 2MS medium supplemented with kanamycin and Claforan, then, after rooting, transferred into soil and, after cultivation for two weeks, grown in a controlled-environment cabinet or in the greenhouse and allowed to flower, and mature seeds were harvested and analyzed for Δ6-desaturase expression by means of lipid analyses. Lines with increased contents of or double bonds at the Δ6 position were identified. In the stably transformed transgenic lines which functionally expressed the transgene, an increased content of double bonds at position Δ6 was found in comparison with untransformed control plants.

Example 9

Lipid Extraction from Seeds

The plant material was first homogenized mechanically by comminuting in a pestle and mortar to make it more accessible to extraction.

Then, it was boiled for 10 minutes at 100° C. and sedimented after cooling on ice. The cell sediment was hydrolyzed for one hour at 90° C. with 1 N of methanolic sulfuric acid and 2% dimethoxypropane and the lipids were transmethylated. The resulting fatty acid methyl esters (FAMEs) were extracted in petroleum ether. The extracted FAMEs were analyzed by gas liquid chromatography using a capillary column (Chrompack, WCOT Fused Silica, CP-Wax-52 CB, 25 m, 0.32 mm) and a temperature gradient of 170° C. to 240° C. over 20 minutes and 5 minutes at 240° C. The identity of the fatty acid methyl esters was confirmed by comparison with corresponding FAME standards (sigma). The identity and position of the double bond could be analyzed further by suitable chemical derivatization of the FAME mixtures, for example to give 4,4-dimethoxyoxazoline derivatives (Christie, 1997, in: Advances in Lipid Methodology, 4$^{th}$ Edition: Christie, Oily Press, Dundee, 119-169, and 1998, Gaschromatographie-Massenspektrometrie Verfahren [Gas chromatography/mass spectrometry methods], Lipide 33:343-353) using GC-MS. The GC analysis of the fatty acid methyl esters from the transgenic rapeseed which expressed Δ6-desaturase in a seed-specific fashion are shown in Table III. The transgenic rapeseed shows at least 4.95% γ-linolenic acid in the seed.

Table III shows the GC analyses of the fatty acid methyl esters from mature, transgenic rapeseed which expressed Δ6-desaturase in a seed-specific fashion. The fatty acid composition is shown in [mol %] of the overall fatty acids. It car be stated that individual plants of the T2 generation which have been obtained from positively transformed, selfed plants contain up to approx. 4.95% of γ-linolenic acid.

TABLE III

| GC analysis of the oilseed rape fatty acid methyl esters | | | | | | |
| --- | --- | --- | --- | --- | --- | --- |
| Name | 18:0 | 18:1 | 18:2 | 18:3 (γ) | 18:3 (α) | 18:4 |
| R2-T2-11/1a | 1.98 | 53.58 | 22.63 | 3.86 | 11.38 | 0 |
| R2-T2-11/1b | 1.86 | 52.04 | 25.45 | 2.31 | 11.39 | 0 |
| R2-T2-11/1c | 1.95 | 49.17 | 24.30 | 2.84 | 9.20 | 0 |
| R2-T2-11/3 | 1.82 | 49.83 | 24.54 | 3.88 | 10.12 | 0 |
| R2-T2-11/4 | 1.72 | 48.02 | 24.66 | 4.95 | 9.52 | 0 |
| R2-T2-11/5a | 1.73 | 51.98 | 25.27 | 4.27 | 9.61 | 0 |
| R2-T2-11/5b | 2.02 | 56.19 | 25.08 | 0 | 9.33 | 0 |
| R2-T2-11/5c | 2.01 | 46.95 | 27.38 | 0 | 10.37 | 0 |
| R2-T2-11/5d | 1.83 | 49.49 | 24.15 | 4.40 | 8.65 | 0 |
| R2-T2-11/6 | 2.08 | 54.52 | 23.94 | 2.05 | 9.29 | 0 |
| R2-T2-11/10 | 1.94 | 53.92 | 22.81 | 4.06 | 9.44 | 0 |
| R2-T2-WT | 1.90 | 47.75 | 30.91 | 0 | 10.51 | 0 |

We claim:

1. A process of preparing an unsaturated fatty acid, which comprises introducing, into an organism being a yeast or a monocot or dicot plant, at least one nucleic acid sequence encoding a polypeptide having Δ6-desaturase activity, selected from the group consisting of:
   a) a nucleic acid sequence having the sequence shown in SEQ ID NO: 1,
   b) a nucleic acid sequence encoding a polypeptide having the amino acid sequence shown in SEQ ID NO: 2, and
   c) a nucleic acid sequence encoding a polypeptide having at least 90% sequence identity at the amino acid level with the amino acid sequence shown in SEQ ID NO: 2,
   and culturing the organism to express said polypeptide.

2. The process of claim 1, wherein the organism is a monocot or dicot plant.

3. The process of claim 1, wherein the organism is an oil seed crop plant.

4. The process of claim 1, wherein the unsaturated fatty acid is isolated from the organism.

5. A transgenic organism selected from the group consisting of a yeast, a monocot plant and a dicot plant, the organism comprising at least one nucleic acid sequence encoding a polypeptide with Δ6-desaturase activity, selected from the group consisting of:
   a) a nucleic acid sequence having the sequence shown in SEQ ID NO: 1,
   b) a nucleic acid sequence encoding a polypeptide having the amino acid sequence shown in SEQ ID NO: 2, and
   c) a nucleic acid sequence encoding a polypeptide having at least 90% sequence identity at the amino acid level with the amino acid sequence shown in SEQ ID NO: 2.

6. The transgenic organism of claim 5, wherein the organism is a monocot plant or a dicot plant.

7. The transgenic organism of claim 5, wherein the organism is an oil seed crop plant.

* * * * *

SEQUENCE LISTING

<160> NUMBER OF SEQ ID NOS: 13

<210> SEQ ID NO 1
<211> LENGTH: 2012
<212> TYPE: DNA
<213> ORGANISM: Physcomitrella patens
<220> FEATURE:
<221> NAME/KEY: CDS
<222> LOCATION: (319)..(1896)

<400> SEQUENCE: 1

| | |
|---|---|
| ccgagtcgcg gatcagccat cgcccgccca gggccgcctg cattgtgtgg gacggtgttg | 60 |
| gaggaggagg cagatgcgcg ggcgttggtg gagtcgtcat ccgaggatct actgcggcaa | 120 |
| tacctccggg ttttggagcg ggcaaactct gttgcggctc ggaaggctat aggttcggca | 180 |
| ggagactgtt gattttatgt cggggggcatt gccattgtgg agagcggggg agactcagga | 240 |
| tctgtgagtg tgcgtgcagc gccccgactg ccgcagagcg tctgtgtatg acgaggttgt | 300 |

| | | |
|---|---|---|
| tgtggagcgg cttttgaa atg gta ttc gcg ggc ggt gga ctt cag cag ggc | | 351 |
| Met Val Phe Ala Gly Gly Gly Leu Gln Gln Gly | | |
| 1 5 10 | | |

| | | |
|---|---|---|
| tct ctc gaa gaa aac atc gac gtc gag cac att gcc agt atg tct ctc | | 399 |
| Ser Leu Glu Glu Asn Ile Asp Val Glu His Ile Ala Ser Met Ser Leu | | |
| 15 20 25 | | |

| | | |
|---|---|---|
| ttc agc gac ttc ttc agt tat gtg tct tca act gtt ggt tcg tgg agc | | 447 |
| Phe Ser Asp Phe Phe Ser Tyr Val Ser Ser Thr Val Gly Ser Trp Ser | | |
| 30 35 40 | | |

| | | |
|---|---|---|
| gta cac agt ata caa cct ttg aag cgc ctg acg agt aag aag cgt gtt | | 495 |
| Val His Ser Ile Gln Pro Leu Lys Arg Leu Thr Ser Lys Lys Arg Val | | |
| 45 50 55 | | |

| | | |
|---|---|---|
| tcg gaa agc gct gcc gtg caa tgt ata tca gct gaa gtt cag aga aat | | 543 |
| Ser Glu Ser Ala Ala Val Gln Cys Ile Ser Ala Glu Val Gln Arg Asn | | |
| 60 65 70 75 | | |

| | | |
|---|---|---|
| tcg agt acc cag gga act gcg gag gca ctc gca gaa tca gtc gtg aag | | 591 |
| Ser Ser Thr Gln Gly Thr Ala Glu Ala Leu Ala Glu Ser Val Val Lys | | |
| 80 85 90 | | |

| | | |
|---|---|---|
| ccc acg aga cga agg tca tct cag tgg aag aag tcg aca cac ccc cta | | 639 |
| Pro Thr Arg Arg Arg Ser Ser Gln Trp Lys Lys Ser Thr His Pro Leu | | |
| 95 100 105 | | |

| | | |
|---|---|---|
| tca gaa gta gca gta cac aac aag cca agc gat tgc tgg att gtt gta | | 687 |
| Ser Glu Val Ala Val His Asn Lys Pro Ser Asp Cys Trp Ile Val Val | | |
| 110 115 120 | | |

| | | |
|---|---|---|
| aaa aac aag gtg tat gat gtt tcc aat ttt gcg gac gag cat ccc gga | | 735 |
| Lys Asn Lys Val Tyr Asp Val Ser Asn Phe Ala Asp Glu His Pro Gly | | |
| 125 130 135 | | |

| | | |
|---|---|---|
| gga tca gtt att agt act tat ttt gga cga gac ggc aca gat gtt ttc | | 783 |
| Gly Ser Val Ile Ser Thr Tyr Phe Gly Arg Asp Gly Thr Asp Val Phe | | |
| 140 145 150 155 | | |

| | | |
|---|---|---|
| tct agt ttt cat gca gct tct aca tgg aaa att ctt caa gac ttt tac | | 831 |
| Ser Ser Phe His Ala Ala Ser Thr Trp Lys Ile Leu Gln Asp Phe Tyr | | |
| 160 165 170 | | |

| | | |
|---|---|---|
| att ggt gac gtg gag agg gtg gag ccg act cca gag ctg ctg aaa gat | | 879 |
| Ile Gly Asp Val Glu Arg Val Glu Pro Thr Pro Glu Leu Leu Lys Asp | | |
| 175 180 185 | | |

| | | |
|---|---|---|
| ttc cga gaa atg aga gct ctt ttc ctg agg gag caa ctt ttc aaa agt | | 927 |
| Phe Arg Glu Met Arg Ala Leu Phe Leu Arg Glu Gln Leu Phe Lys Ser | | |
| 190 195 200 | | |

| | | |
|---|---|---|
| tcg aaa ttg tac tat gtt atg aag ctg ctc acg aat gtt gct att ttt | | 975 |
| Ser Lys Leu Tyr Tyr Val Met Lys Leu Leu Thr Asn Val Ala Ile Phe | | |
| 205 210 215 | | |

-continued

```
gct gcg agc att gca ata ata tgt tgg agc aag act att tca gcg gtt      1023
Ala Ala Ser Ile Ala Ile Ile Cys Trp Ser Lys Thr Ile Ser Ala Val
220             225                 230                 235 ttg gct tca gct tgt atg atg gct ctg tgt ttc caa cag tgc gga tgg      1071
Leu Ala Ser Ala Cys Met Met Ala Leu Cys Phe Gln Gln Cys Gly Trp
                240                 245                 250 cta tcc cat gat ttt ctc cac aat cag gtg ttt gag aca cgc tgg ctt      1119
Leu Ser His Asp Phe Leu His Asn Gln Val Phe Glu Thr Arg Trp Leu
            255                 260                 265 aat gaa gtt gtc ggg tat gtg atc ggc aac gcc gtt ctg ggg ttt agt      1167
Asn Glu Val Val Gly Tyr Val Ile Gly Asn Ala Val Leu Gly Phe Ser
        270                 275                 280 aca ggg tgg tgg aag gag aag cat aac ctt cat cat gct gct cca aat      1215
Thr Gly Trp Trp Lys Glu Lys His Asn Leu His His Ala Ala Pro Asn
    285                 290                 295 gaa tgc gat cag act tac caa cca att gat gaa gat att gat act ctc      1263
Glu Cys Asp Gln Thr Tyr Gln Pro Ile Asp Glu Asp Ile Asp Thr Leu
300                 305                 310                 315 ccc ctc att gcc tgg agc aag gac ata ctg gcc aca gtt gag aat aag      1311
Pro Leu Ile Ala Trp Ser Lys Asp Ile Leu Ala Thr Val Glu Asn Lys
                320                 325                 330 aca ttc ttg cga atc ctc caa tac cag cat ctg ttc ttc atg ggt ctg      1359
Thr Phe Leu Arg Ile Leu Gln Tyr Gln His Leu Phe Phe Met Gly Leu
            335                 340                 345 tta ttt ttc gcc cgt ggt agt tgg ctc ttt tgg agc tgg aga tat acc      1407
Leu Phe Phe Ala Arg Gly Ser Trp Leu Phe Trp Ser Trp Arg Tyr Thr
        350                 355                 360 tct aca gca gtg ctc tca cct gtc gac agg ttg ttg gag aag gga act      1455
Ser Thr Ala Val Leu Ser Pro Val Asp Arg Leu Leu Glu Lys Gly Thr
    365                 370                 375 gtt ctg ttt cac tac ttt tgg ttc gtc ggg aca gcg tgc tat ctt ctc      1503
Val Leu Phe His Tyr Phe Trp Phe Val Gly Thr Ala Cys Tyr Leu Leu
380                 385                 390                 395 cct ggt tgg aag cca tta gta tgg atg gcg gtg act gag ctc atg tcc      1551
Pro Gly Trp Lys Pro Leu Val Trp Met Ala Val Thr Glu Leu Met Ser
                400                 405                 410 ggc atg ctg ctg ggc ttt gta ttt gta ctt agc cac aat ggg atg gag      1599
Gly Met Leu Leu Gly Phe Val Phe Val Leu Ser His Asn Gly Met Glu
            415                 420                 425 gtt tat aat tcg tct aaa gaa ttc gtg agt gca cag atc gta tcc aca      1647
Val Tyr Asn Ser Ser Lys Glu Phe Val Ser Ala Gln Ile Val Ser Thr
        430                 435                 440 cgg gat atc aaa gga aac ata ttc aac gac tgg ttc act ggt ggc ctt      1695
Arg Asp Ile Lys Gly Asn Ile Phe Asn Asp Trp Phe Thr Gly Gly Leu
    445                 450                 455 aac agg caa ata gag cat cat ctt ttc cca aca atg ccc agg cat aat      1743
Asn Arg Gln Ile Glu His His Leu Phe Pro Thr Met Pro Arg His Asn
460                 465                 470                 475 tta aac aaa ata gca cct aga gtg gag gtg ttc tgt aag aaa cac ggt      1791
Leu Asn Lys Ile Ala Pro Arg Val Glu Val Phe Cys Lys Lys His Gly
                480                 485                 490 ctg gtg tac gaa gac gta tct att gct acc ggc act tgc aag gtt ttg      1839
Leu Val Tyr Glu Asp Val Ser Ile Ala Thr Gly Thr Cys Lys Val Leu
            495                 500                 505 aaa gca ttg aag gaa gtc gcg gag gct gcg gca gag cag cat gct acc      1887
Lys Ala Leu Lys Glu Val Ala Glu Ala Ala Ala Glu Gln His Ala Thr
        510                 515                 520
```

```
acc agt taa cagtctttgg aaagcttggc aattgatctt tattctccac          1936
Thr Ser
    525 ggcagttgct tgtttgtttt ggggtgaatg accgaatgta ctggcatcca ttcttctgta 1996 gccatcaatt ttgaac                                                 2012
```

<210> SEQ ID NO 2
<211> LENGTH: 525
<212> TYPE: PRT
<213> ORGANISM: Physcomitrella patens

<400> SEQUENCE: 2

```
Met Val Phe Ala Gly Gly Gly Leu Gln Gln Gly Ser Leu Glu Glu Asn
 1               5                  10                  15

Ile Asp Val Glu His Ile Ala Ser Met Ser Leu Phe Ser Asp Phe Phe
            20                  25                  30

Ser Tyr Val Ser Ser Thr Val Gly Ser Trp Ser Val His Ser Ile Gln
        35                  40                  45

Pro Leu Lys Arg Leu Thr Ser Lys Lys Arg Val Ser Glu Ser Ala Ala
    50                  55                  60

Val Gln Cys Ile Ser Ala Glu Val Gln Arg Asn Ser Ser Thr Gln Gly
65                  70                  75                  80

Thr Ala Glu Ala Leu Ala Glu Ser Val Val Lys Pro Thr Arg Arg Arg
                85                  90                  95

Ser Ser Gln Trp Lys Lys Ser Thr His Pro Leu Ser Glu Val Ala Val
            100                 105                 110

His Asn Lys Pro Ser Asp Cys Trp Ile Val Lys Asn Lys Val Tyr
        115                 120                 125

Asp Val Ser Asn Phe Ala Asp Glu His Pro Gly Gly Ser Val Ile Ser
    130                 135                 140

Thr Tyr Phe Gly Arg Asp Gly Thr Asp Val Phe Ser Ser Phe His Ala
145                 150                 155                 160

Ala Ser Thr Trp Lys Ile Leu Gln Asp Phe Tyr Ile Gly Asp Val Glu
                165                 170                 175

Arg Val Glu Pro Thr Pro Glu Leu Leu Lys Asp Phe Arg Glu Met Arg
            180                 185                 190

Ala Leu Phe Leu Arg Glu Gln Leu Phe Lys Ser Ser Lys Leu Tyr Tyr
        195                 200                 205

Val Met Lys Leu Leu Thr Asn Val Ala Ile Phe Ala Ala Ser Ile Ala
    210                 215                 220

Ile Ile Cys Trp Ser Lys Thr Ile Ser Ala Val Leu Ala Ser Ala Cys
225                 230                 235                 240

Met Met Ala Leu Cys Phe Gln Gln Cys Gly Trp Leu Ser His Asp Phe
                245                 250                 255

Leu His Asn Gln Val Phe Glu Thr Arg Trp Leu Asn Glu Val Val Gly
            260                 265                 270

Tyr Val Ile Gly Asn Ala Val Leu Gly Phe Ser Thr Gly Trp Trp Lys
        275                 280                 285

Glu Lys His Asn Leu His Ala Ala Pro Asn Glu Cys Asp Gln Thr
    290                 295                 300

Tyr Gln Pro Ile Asp Glu Asp Ile Asp Thr Leu Pro Leu Ile Ala Trp
305                 310                 315                 320

Ser Lys Asp Ile Leu Ala Thr Val Glu Asn Lys Thr Phe Leu Arg Ile
                325                 330                 335
```

```
Leu Gln Tyr Gln His Leu Phe Phe Met Gly Leu Leu Phe Phe Ala Arg
            340                 345                 350

Gly Ser Trp Leu Phe Trp Ser Trp Arg Tyr Thr Ser Thr Ala Val Leu
        355                 360                 365

Ser Pro Val Asp Arg Leu Leu Glu Lys Gly Thr Val Leu Phe His Tyr
    370                 375                 380

Phe Trp Phe Val Gly Thr Ala Cys Tyr Leu Leu Pro Gly Trp Lys Pro
385                 390                 395                 400

Leu Val Trp Met Ala Val Thr Glu Leu Met Ser Gly Met Leu Leu Gly
                405                 410                 415

Phe Val Phe Val Leu Ser His Asn Gly Met Glu Val Tyr Asn Ser Ser
                420                 425                 430

Lys Glu Phe Val Ser Ala Gln Ile Val Ser Thr Arg Asp Ile Lys Gly
                435                 440                 445

Asn Ile Phe Asn Asp Trp Phe Thr Gly Gly Leu Asn Arg Gln Ile Glu
            450                 455                 460

His His Leu Phe Pro Thr Met Pro Arg His Asn Leu Asn Lys Ile Ala
465                 470                 475                 480

Pro Arg Val Glu Val Phe Cys Lys Lys His Gly Leu Val Tyr Glu Asp
                485                 490                 495

Val Ser Ile Ala Thr Gly Thr Cys Lys Val Leu Lys Ala Leu Lys Glu
            500                 505                 510

Val Ala Glu Ala Ala Ala Glu Gln His Ala Thr Thr Ser
            515                 520                 525

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Glu Lys Asp Glu Leu
  1               5

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)
<223> OTHER INFORMATION: Inosine

<400> SEQUENCE: 4
tggtggaart ggamncayaa                                                20

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: a, c, g, or t
```

<400> SEQUENCE: 5
ggraanarrt grtgytc                                                17

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccgagtcgcg gatcagcc                                               18

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cagtacattc ggtcattcac c                                           21

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccgctcgagc gaggttgttg tggagcggc                                   29

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctgaaatagt cttgctcc                                               18

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccggtaccaa aatggtattc gcgggcggtg                                  30

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 11
ccggtacctt aactggtggt agcatgct                                         28

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtcgacccgc ggactagtgg gccctctaga cccgggggat ccggatctgc tggctatgaa      60

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Asp Glu Leu
  1
```